United States Patent
Mjalli et al.

(10) Patent No.: US 11,525,116 B2
(45) Date of Patent: Dec. 13, 2022

(54) DATE PALM MEDIUM COMPOSITIONS AND METHODS

(71) Applicant: Bien-Etre Labs, LLC, High Point, NC (US)

(72) Inventors: Adnan Mjalli, High Point, NC (US); Salam A. Ibrahim, High Point, NC (US)

(73) Assignee: Bien-Etre Labs, LLC, High Point, NC (US)

(*) Notice: Subject to any disclaimer, the term of this patent is extended or adjusted under 35 U.S.C. 154(b) by 275 days.

(21) Appl. No.: 16/387,274

(22) Filed: Apr. 17, 2019

(65) Prior Publication Data

US 2019/0316080 A1    Oct. 17, 2019

Related U.S. Application Data

(60) Provisional application No. 62/658,916, filed on Apr. 17, 2018.

(51) Int. Cl.
*C12N 1/20* (2006.01)
*A23L 33/135* (2016.01)

(52) U.S. Cl.
CPC .............. *C12N 1/20* (2013.01); *A23L 33/135* (2016.08); *A23V 2002/00* (2013.01); *A23Y 2220/67* (2013.01); *A23Y 2220/71* (2013.01); *A23Y 2220/73* (2013.01); *A23Y 2300/21* (2013.01); *A23Y 2300/25* (2013.01); *A23Y 2300/55* (2013.01); *C12N 2500/76* (2013.01)

(58) Field of Classification Search
CPC ............................... C12N 1/20; C12N 2500/76
See application file for complete search history.

(56) References Cited

U.S. PATENT DOCUMENTS

| | | | |
|---|---|---|---|
| 5,853,488 A | 12/1998 | Silver | |
| 2003/0232422 A1 | 12/2003 | Gerber et al. | |
| 2016/0058805 A1 | 3/2016 | Majeed et al. | |
| 2019/0316080 A1 | 10/2019 | Mjalli et al. | |

FOREIGN PATENT DOCUMENTS

| | | |
|---|---|---|
| WO | 9530027 | 11/1995 |
| WO | 2019/204494 | 10/2019 |

OTHER PUBLICATIONS

Al-Taweil et al., "Use of date syrup as alternative carbon source for microbial cultivation", World Journal of Microbiology, vol. 2(1), pp. 022-025, Aug. 2015 (Year: 2015).*
Davis et al., "Effects of Growth Medium, Inoculum Size, and Incubation Time on Culturability and Isolation of Soil Bacteria", Applied and Environmental Microbiology, Feb. 2005, p. 826-834 (Year: 2005).*
Safar Al-Thubiani et al., "The Prebiotic Properties of Date Palm (*Phoenix dactylifera* L.) Seeds in Stimulating Probiotic Lactobacillus", Journal of Pure and Applied Microbiology, Dec. 2017. vol. 11(4), p. 1675-1686 (Year: 2017).*
PCT/US2019/027939 , "International Search Report and Written Opinion", Oct. 30, 2019, 20 pages.
PCT/US2019/027939 , "Invitation to Pay Additional Fees and, Where Applicable, Protest Fee", Aug. 28, 2019, 12 pages.
Shubbar , "Sugar Extraction from Dates", Date Palm Journal, vol. 1, No. 1, Jul. 1, 1981, pp. 61-78.
PCT/US2019/027939, International Preliminary Report on Patentability, dated Oct. 29, 2020, 13 pages.
PCT/US2019/027939, Notification Concerning Availability of the Re-Publication of the International Application, Dec. 5, 2019, 9 pages.
Elsawey et al., "Plant Broth- (Not Bovine-) Based Culture Media Provide the Most Compatible Vegan Nutrition for in Vitro Culturing and in Situ Probing of Plant Microbiota," Diversity, vol. 12, No. 418, Nov. 4, 2020, 19 pages.
Ferjani et al., "The Date Palm Tree Rhizosphere is a Niche for Plant Growth Promoting Bacteria in the Oasis Ecosystem," Hindawi Publishing Corporation BioMed Research International vol. 2015, Article ID 153851, 2015, 10 pages.
Saleh et al., "A Novel Plant-Based-Sea Water Culture Media for in Vitro Cultivation and in Situ Recovery of the Halophyte Microbiome," Journal of Advanced Research 8, 2017, pp. 577-590.
EP 19722755.6, "Partial Search Report," May 31, 2022, 3 pages.
PCT/US2022/070946, International Search Report and Written Opinion, dated Jun. 9, 2022, 11 pages.

* cited by examiner

*Primary Examiner* — Ruth A Davis
(74) *Attorney, Agent, or Firm* — Kilpatrick Townsend & Stockton LLP

(57) ABSTRACT

Disclosed are date palm compositions and methods of use of such compositions. Such compositions may be used as part of a growth medium for culture of microorganisms. In certain embodiments, date palm extracts of the disclosure are used as part a culture medium to grow Lactobacilli.

5 Claims, 3 Drawing Sheets

DATE PALM MEDIUM COMPOSITIONS AND METHODS

FIELD OF THE INVENTION

This invention relates to date palm compositions and methods of use of such compositions.

BACKGROUND

Lactobacilli are among the most important group of bacteria in applied microbiology. *Lactobacillus* is a genus of Gram-positive, facultative anaerobic, rod-shaped, non-spore-forming bacteria and is a major part of the lactic acid bacteria group that converts sugars into lactic acid. In humans, lactobacilli constitute a significant component of the microbiota in a number of body systems, including the digestive, urinary, and genital systems. Lactobacilli exhibit a symbiotic relationship with the human body as they protect the host against potential invasions by pathogens, and, in turn, the host provides a source of nutrients necessary for bacterial growth. *Lactobacillus* is the most common probiotic found in foods, including yogurt, and is diverse in its application to maintain human well-being as it can help treat diarrhea, vaginal infections and skin disorders, including eczema.

Formulating cultivation media for lactobacilli is very challenging as lactobacilli are fastidious bacteria, and their nutritional requirements can vary widely depending on the strain. Growth of *lactobacillus* species requires carbohydrates, amino acids, vitamins, and minerals. For normal growth, culture media are supplemented with various free amino acids, peptides, nucleic acid derivatives, fatty acid esters, minerals, vitamins, and buffering agents in addition to sugar. Nitrogen sources such as soy peptones, peptones of animal origin, bactopeptone, triptone, and beef extract or yeast extract form an essential part of *Lactobacillus* media. These nitrogen sources are rich in diversified free amino acids, peptides, and most of the required vitamins and minerals, but they are expensive and thus constitute a significant portion of media costs. For example, the most commonly used media for growth of *Lactobacillus* spp. is DeMan Rogosa Sharpe (MRS) media, which typically contains glucose, yeast and meat extracts, casein peptones, and salts and is therefore expensive to produce. Consequently, a low cost alternative medium would be beneficial. Replacing expensive nitrogen sources with lower cost ingredients such as food or agricultural byproducts could prove useful. Other bacteria (e.g., *Bifidobacterium* spp., *Campylobacter* spp., *Helicobacter* spp, can require similar adjustments to media to promote optimal growth.

Dates are an abundant agricultural product and play a major role in human nutrition as well as the food industry. Dates are a rich source of carbohydrates (mainly starch and sugars), some amino acids, vitamins (vitamin A, vitamin C, thiamin (B1), riboflavin (B2), niacin, and vitamin E), minerals (calcium, iron, magnesium, phosphorus, potassium, sodium, and zinc), dietary fiber, and also contain other minor nutrients such as antioxidants, triglycerides, linoleic acid, and palmitic acid. However, the date fruit industry produces a large amount of waste due to unwanted byproducts. Each year, more than 55,000 tons of dates are wasted due to low quality and/or unusable byproducts. The nutritional compositions of date byproducts allow them to be utilized to develop growth media for cultivating a variety of microorganisms.

Dietary fiber content of dates can further contribute to their nutritional significance as dates can be used in the preparation of fiber-based foods and dietary supplements. Dates contain both soluble and insoluble fibers. The main component is cellulose, hemicelluloses, pectin, and lignin. The lignin composition is divided into low- and high-lignin separated from palm date fibers. High-lignin fibers contain 75% lignin and 15.8% polysaccharide, while the low-lignin fibers contain 27.2% lignin and 53.1% polysaccharides. Palm date fiber consists of 54% high-lignin fiber and 46% low-lignin fiber. In dates, insoluble fiber is the major component of dietary fiber; on the other hand, soluble pectin continues to accumulate regularly until the date fruit reaches the Rutab (ripened) stage.

Disclosed herein is a novel preparation of date palm extract (DPE) broth that can be applied to utilize the nutritional benefits of date palms for cultivating microorganisms.

SUMMARY

Embodiments of the invention comprise compositions and methods for cultivating microorganisms. The invention may be embodied in a variety of ways. In some aspects, the invention comprises a method of preparing a date palm extract (DPE) broth comprising: (i) obtaining a mass of date material; (ii) combining the date material with a suspension liquid to produce a slurry mixture; (iii) processing the slurry mixture to produce a date palm extract broth with fibers (DPEF); and (iv) separating the DPEF into the DPE broth and a mass of date palm fiber (DPF).

In other aspects, the invention comprises a method for preparing date palm medium (DPM) for culturing microorganisms comprising: (i) preparing a buffer solution; (ii) buffering a date palm extract (DPE) broth with the buffer solution, wherein the DPE broth is prepared according to the method as described herein; and (iii) adding a nitrogen source from non-animal origin to the buffered DPE broth. In one embodiment, the method of preparing DPE broth comprises: (i) obtaining a mass of date material; (ii) combining the date material with a suspension liquid to produce a slurry mixture; (iii) processing the slurry mixture to produce a date palm extract broth with fibers (DPEF); and (iv) separating the DPEF into the DPE broth and a mass of date palm fiber (DPF).

In another aspect, the invention comprises a method for preparing a date palm medium with fiber (DPFM) for culturing microorganisms comprising: (i) preparing a buffer solution; (ii) buffering a date palm extract (DPE) broth with the buffer solution, wherein the DPE broth is prepared according to the method as described herein; (iii) adding an amount of date palm fiber (DPF), wherein the DPF is isolated according to the method as described herein, and (iv) adding a nitrogen source from a non-animal origin to the buffered DPE broth. In one embodiment, the method of preparing a DPE broth comprises: (i) obtaining a mass of date material; (ii) combining the date material with a suspension liquid to produce a slurry mixture; (iii) processing the slurry mixture to produce a date palm extract broth with fibers (DPEF); and (iv) separating the DPEF into the DPE broth and a mass of date palm fiber (DPF).

In another embodiment, the method of isolating DPF comprises: (i) obtaining a mass of date fruit; (ii) applying an amount of pressure to the date fruit to extract liquid therefrom and form a date presscake; (iii) combining the date presscake with a suspension liquid to produce a slurry mixture; (iv) processing the slurry mixture; and (v) separating the slurry mixture into the DPE broth and a mass of date palm fiber (DPF).

In yet another aspect, the invention comprises a method of preparing a date palm medium with fiber (DPFM) for culturing microorganisms comprising: (i) preparing a buffer solution; (ii) buffering a date palm extract broth with fibers (DPEF) with the buffer solution, wherein the DPEF is prepared according to the method as described herein; and (iii) adding a nitrogen source from non-animal origin to the buffered DPEF.

In another aspect, the invention comprises a composition of a medium for culturing microorganisms that may comprise a buffered date palm extract (DPE) and a nitrogen source. In still other aspects, the invention comprises a composition for cultivating microorganisms comprising DPM.

In other aspects, the invention comprises composition of a medium for culturing microorganisms that may comprise a buffered date palm extract (DPE), wherein the DPE is prepared according to the method as described above, an amount of date palm fiber (DPF), wherein the DPF is isolated according to the method as described herein, and a nitrogen source. In still other aspects, the invention comprises a composition for cultivating microorganisms comprising DPFM. In yet another aspect, provided is a method of preparing a date palm medium with fiber (DPFM) for cultivating microorganisms comprising: (i) preparing a buffer solution, (ii) buffering a date palm extract broth with fibers (DPEF) with the buffer solution, wherein the DPEF is prepared according to the methods described herein, and (iii) adding a nitrogen source of non-animal origin to the buffered DPEF.

In one embodiment, the method of preparing DPE broth comprises: (i) obtaining a mass of date fruit; (ii) applying an amount of pressure to the date fruit to extract liquid therefrom and form a date presscake; (iii) combining the date presscake with a suspension liquid to produce a slurry mixture; (iv) processing the slurry mixture; and (v) separating the slurry mixture into the DPE broth and a mass of date palm fiber (DPF). In another embodiment, the method of isolating DPF comprises: (i) obtaining a mass of date fruit; (ii) applying an amount of pressure to the date fruit to extract liquid therefrom and form a date presscake; (iii) combining the date presscake with a suspension liquid to produce a slurry mixture; (iv) processing the slurry mixture; and (v) separating the slurry mixture into the DPE broth and a mass of date palm fiber (DPF).

In other aspects, the invention comprises a method for cultivating microorganisms comprising: (i) inoculating a date palm medium (DPM) with microorganisms; and (ii) incubating the microorganisms under conditions such that growth occurs. In another aspect, the invention comprises, a probiotic comprising bacteria cultivated in DPM.

In another aspect, the invention comprises a method for cultivating microorganisms comprising: (i) inoculating a date palm medium with fiber (DPFM) with microorganisms; and (ii) incubating the microorganisms under conditions such that growth occurs. In another aspect, the invention comprises, a probiotic comprising bacteria cultivated in DPFM.

BRIEF DESCRIPTION OF THE FIGURES

The present invention may be better understood by referring to the following non-limiting figures.

DETAILED DESCRIPTION OF THE INVENTION

Terms and Definitions

Figure 1:
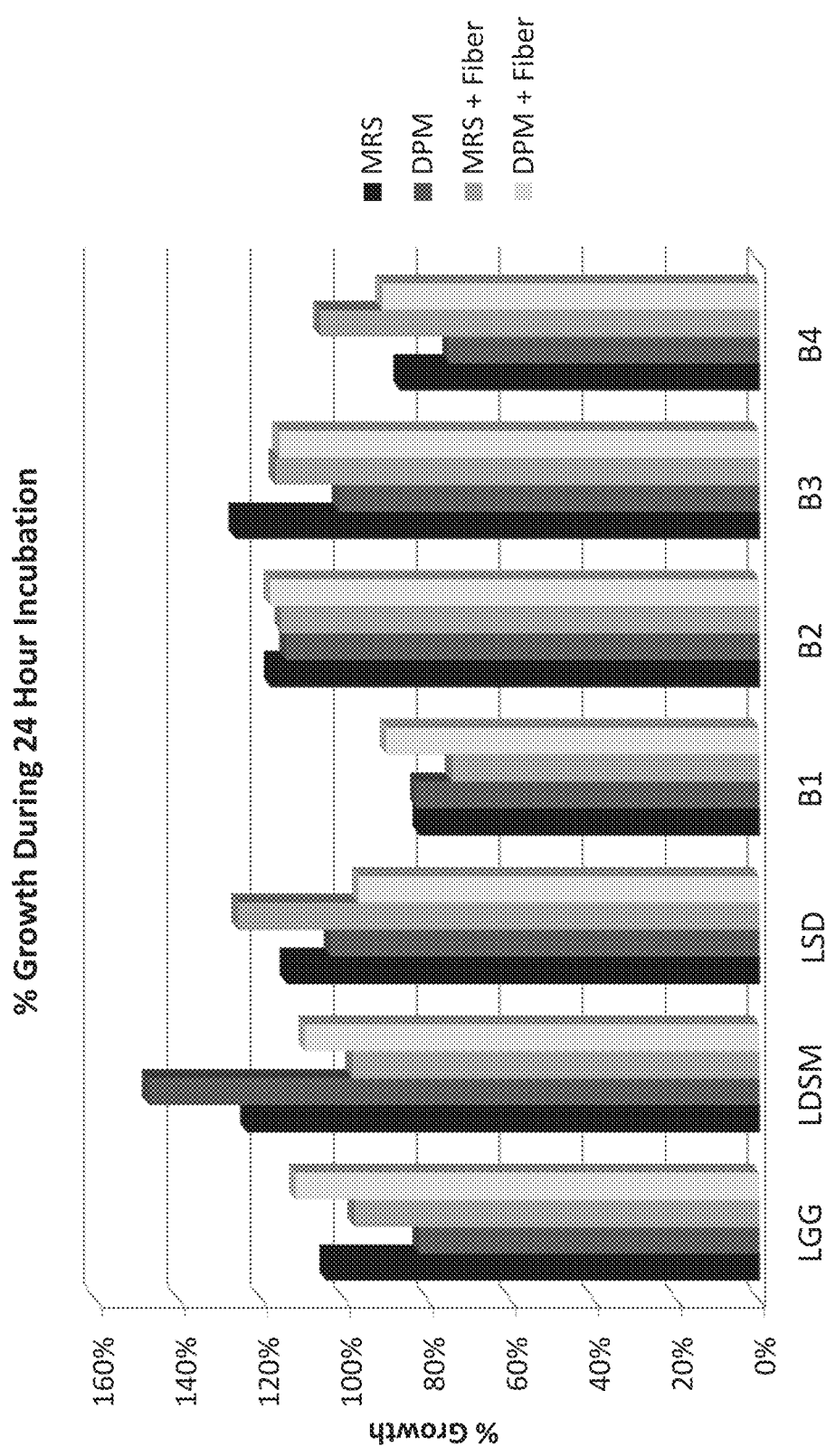
FIG. 1 shows the percent growth of a variety of bacteria: *Lactobacillus rhamnosus* (LGG), *Lactobacillus reuteri* DSM (LDSM), *Lactobacillus reuteri* SD (LSD), *Bifidobacterium bifidum* (B1), *Bifidobacterium bifidum* (B2), *Bifidobacterium animalis* (B3), and *Bifidobacterium longum* (B4) on differing media: De Man, Rogosa and Sharpe medium (MRS), date palm medium (DPM), De Man, Rogosa and Sharpe medium+fiber (MRSF), and date palm medium+fiber (DPFM) following a 24 hour incubation in accordance with an embodiment of the disclosure. The first bar in each bacteria group represents bacteria grown in MRS media. The second bar in each bacteria group represents bacteria grown in DPM. The third bar in each bacteria group represents bacteria grown in MRS+Fiber media. The fourth bar in each bacteria group represents bacteria grown in DPM+Fiber media.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more, e.g. 1 to 6.1, and ending with a maximum value of 10 or less, e.g., 5.5 to 10. Additionally, any reference referred to as being "incorporated herein" is to be understood as being incorporated in its entirety.

It is further noted that, as used in this specification, the singular forms "a," "an," and "the" include plural referents unless expressly and unequivocally limited to one referent. The term "and/or" generally is used to refer to at least one or the other. In some case the term "and/or" is used interchangeably with the term "or." The term "including" is used herein to mean, and is used interchangeably with, the phrase "including but not limited to." The term "such as" is used herein to mean, and is used interchangeably with, the phrase "such as but not limited to."

Method of Preparing Date Palm Extract Broth

In another aspect, the methods of preparing date palm medium (DPM) as provided herein include methods for preparing date palm extract (DPE) broth.

The method comprises the steps of: (i) obtaining a mass of date fruit; (ii) applying an amount of pressure to the date fruit to extract liquid therefrom and form a date presscake; (iii) combining the date presscake with a suspension liquid to produce a slurry mixture; (iv) processing the slurry mixture; and (v) separating the slurry mixture into the DPE broth and a mass of date palm fiber (DPF).

The fruit of the date palm (*Phoenix dactylifera* L.) is one of the most widely grown fruits in the world, typically, planted in hot dry regions. However, large amounts of dates end up as byproducts or waste. Date fruit progress through five stages of maturation: (1) Hababouk (2) Kimiri; (3) Khalal; (4) Rutab; and (5) Tamar. Dates are primarily composed of water, sugar, protein, fat, pectin, minerals, vitamins, crude fiber, antioxidants, and polyphenols. As dates mature, the moisture and sugar contents change. For example, unripe Khalal dates are 50% moisture while, mature Tamar dates have 10-30% moisture content. In some embodiments, the date fruit is a Tamar date. Tamar dates have reached commercial maturity and the fruit has lost significant amounts of water, which prevents fermentation and ensures conservation of the fruit. Tamar dates are used commercially to produce a variety of date products (e.g., juice, syrup, jam, and jelly). In some embodiments, the date fruit is a commercial byproduct of a Tamar date processing.

Differing date cultivars are also characterized by varying levels of moisture, protein, glucose, fructose, sucrose, and fiber. In certain embodiments, a specific cultivar of dates is used. The date cultivar may be Barhi, Deglet Noor, Fard. Hallawi, Khardragy, Khalas, Khasab, Lulu, Madjool, or Zahidi, or any combination thereof. In some embodiments, multiple date cultivars may be used. In an embodiment, DPE solution is prepared from Khalas dates. Khalas dates are typically composed of about 36% glucose, about 32% fructose and <0.05% sucrose.

Dates contain both soluble and insoluble fibers. The main component is cellulose, hemicelluloses, pectin, and lignin. The lignin composition is divided into low- and high-lignin separated from palm date fibers. High-lignin fibers contain 75% lignin and 15.8% polysaccharide, while the low-lignin fibers contain 27.2% lignin and 53.1% polysaccharides. Palm date fiber consists of 54% high-lignin fiber and 46% low-lignin fiber. In dates, insoluble fiber is the major component of dietary fiber; on the other hand, soluble pectin continues to accumulate regularly until the date fruit reaches the Rutab (ripened) stage.

A number of commercial products can be made from dates. Semi-finished products include date paste, extruded date, diced date, and date powder. Dates may also undergo a preservation process to produce products, including pickles, jellies, and jams. A variety of products can also be derived from dates, including date juice and date syrup. There are three main byproducts from date fruit processing: low-grade rejected dates, date pits, and date presscake. The present invention can utilize two of these byproducts—low-grade rejected dates and date presscake. Low-grade dates are often characterized as having an improper appearance or being undersized, but retain their nutritive components, including sugars, proteins, minerals, and fibers. As such, in some embodiments, the date fruit may be low-grade rejected dates.

Date presscake is a byproduct from the processing of dates to produce derived date products, including date juice and date syrup. When dates are pressed to express the liquid from the flesh of the date, the remaining byproduct of flesh and fiber is the date presscake. Date presscakes retain some nutritive components, including reducing sugars (sucrose, glucose, and fructose), amino acids, fiber, vitamins, and minerals. These nutrients are essential for promoting the growth of some bacteria (e.g., *Lactobacillus* spp.). In some embodiments, the date presscake may be separated into DPE broth and DPF. In some embodiments, the presscake used is a byproduct of processing dates to produce derived date products, including date juice and date syrup.

In some embodiments, the method of preparing a DPE broth comprises: (i) obtaining a mass of date material; (ii) combining the date material with a suspension liquid to produce a slurry mixture; (iii) processing the slurry mixture; and (iv) separating the slurry mixture into the DPE broth and a mass of date palm fibers (DPF).

In some embodiments, the date material comprises a date paste. In other embodiments, the date material comprises a date presscake. In still other embodiments, the date material comprises a date fruit. In some instances the date material is processed prior to being combined with a suspension liquid. For example, the date material may be diced to enhance the extraction mechanism.

In certain instances, the date material comprises a date presscake. In some embodiments, the method of preparing a DPE comprises preparing a date presscake. In certain instances, a date presscake is prepared by obtaining a mass of date fruit. In further embodiments, dates may be processed prior to pressing the dates. For example, dates may be extruded, diced, crushed, and/or macerated to enhance the extraction mechanism and decrease the time required to extract liquid and form a date presscake. In certain instances, pits may be removed from the dates. Alternatively, whole dates may be introduced into the compression area without first altering the dates. Dates may be weighed and sorted by size to ensure the dates fit within the compression area.

In some embodiments, the method of preparing a date presscake comprises, introducing the mass of date fruit into a compression area. In certain embodiments, the compression area is a mechanical press. Generally, a mechanical press is comprised of two basic components: a solid frame, where the materials to be pressed are contained, and a moveable part that can apply pressure. In some embodiments, the compression area is a fruit press. A variety of fruit presses are known in the art and can be used in accordance with the methods of this invention. In certain instances, a batch press may be used. A batch press may comprise a moveable platen, which is pressed into a perforated cylinder containing the fruit. The batch fruit press may be a tank press or a ram press. In alternative embodiments, a continuous press may be used. Types of continuous presses include, but are not limited to roller presses, belt presses, and screw presses.

In some embodiments, the method of preparing a date presscake comprises, applying an amount of pressure to the date fruit to extract liquid therefrom and form a date presscake. The amount of pressure applied and the length of time for which the pressure is applied depends on the type of press used and maturation stage of the date fruit. In some embodiments, the amount of pressure is from about 350-400 psi. In some embodiments, dates are pressed for at least 2 days, at least 3 days, at least 4 days, at least 5 days, at least 6 days, at least 7 days, at least 8 days, at least 9 days, at least 10 days, at least 11 days, or at least 12 days.

In certain embodiments, the date pits are removed from the presscake. The pressure applied to the dates helps to mechanically separate pits from the date presscake allowing to easier removal. Pits may be manually removed. For this reason, in some embodiments it is preferred to separate the date pits from the presscake and not from the whole dates prior to pressing.

In some embodiments the method of preparing a DPE broth comprises combining the date paste with a suspension liquid to produce a slurry mixture. In certain embodiments, the suspension liquid is water or any other liquid generally known in the art. In some embodiments, the suspension liquid is deionized (DI) water. In certain embodiments, the date paste is mixed with DI water in a ratio (paste mass:

suspension liquid volume) from about 1:15 to 1:20, more preferably from about 1.2:10 to 1.2:15, and most preferably from about 1:4 to 1:8.

In some embodiments the method of preparing a DPE broth comprises combining the date paste cubes with a suspension liquid to produce a slurry mixture. In certain embodiments, the suspension liquid is water or any other liquid generally known in the art. In some embodiments, the suspension liquid is deionized (DI) water. In certain embodiments, the date paste cubes are mixed with DI water in a ratio (paste mass:suspension liquid volume) from about 1:1 to 1:5, more preferably from about 1:3 to 2:5, and most preferably from about 1:2 to 2:3. In certain embodiments the date paste cubes mixed with DI water in a preferred ratio may be mixed in a high shear mixer to obtain slurry mixture.

In some embodiments, the method of preparing a DPE broth comprises combining the date presscake with a suspension liquid to produce a slurry mixture. In certain embodiments, the suspension liquid is water or any other liquid generally known in the art. In some embodiments, the suspension liquid is deionized (DI) water. In certain embodiments, the date presscake is mixed with DI water in a ratio (presscake mass:suspension liquid volume) from about 1:1 to 1:5, more preferably from about 1:2 to 1:4, and most preferably from about 1:2.5 to 1:2.8.

In some embodiments, the method of preparing a DPE broth comprises processing the date paste slurry mixture. In some embodiments, the method of preparing a DPE broth comprises processing a date presscake slurry mixture.

In some embodiments, the processing of the date material slurry mixture comprises the processing step comprises at least one heating period, at least one milling period, and at least one soaking period. In certain embodiments, the processing step further includes homogenization at a temperature of at least 40, 45, 50, 55, 60, 65, 70, 75, or 80° C.

Heat treatment can cause the development of Maillard reactions, which are known to inhibit the growth of lactic acid bacteria and prevent high cell mass growth. In some embodiments, processing the slurry mixture comprises multiple heating periods for short periods of time to prevent Maillard reactions. In some instances, the heating period comprises mixing the slurry mixture while it is being heated. In some embodiments, the slurry mixture is heated to at least 50, 55, 60, 65, 70, 75, or 80° C. for at least 0.5, 1.0, 1.5, 2.0, 2.5, 3.0, 3.5, or 4.0 hours. For example, in some embodiments, the slurry mixture is heated in a water bath to a temperature of 60° C. for 3 hours while being mixed.

In some embodiments the milling period comprises milling the heated slurry mixture using a colloid mill. Colloid mills can be used to increase the stability of suspensions and emulsion and to reduce particle size. In some embodiments, a colloid mill is used to reduce the particle size of a solid suspension in a liquid. In some instances, a colloid mill is operated at high speeds (2000-18000 RPM). In some embodiments, the heated slurry mixtures is milled at least one, two, three, four, or five times.

In some embodiments soaking periods are used to extract important nutrients from date palm fiber. In some embodiments the soaking period comprises diluting the milled slurry mixture with the suspension liquid and cooling the diluted, milled slurry mixture to about 4° C. (e.g., 2-8° C.) for at least 12, 13, 14, 15, 16, 17, 18, 19, 20, 21, 22, 23, or 24 hours. For example, in some embodiments the milled slurry mixture is diluted with DI water and cooled to 4° C. for at least 12 hours. In certain embodiments, the suspension liquid is water or any other liquid generally known in the art. In some embodiments, the suspension liquid is deionized (DI) water.

In other embodiments, the processing step may comprise heating, cooling, and mixing the slurry mixture. In certain embodiments, the processing step comprises one or more heating periods and one or more soaking periods.

In certain embodiments, the heating periods comprise heating the slurry mixture to about 70° C. (e.g., 50-80° C.) for about 1 hour (e.g., 0.5-4.0 hours). In some embodiments, the slurry mixture is heated to at least 50, 55, 60, 65, 70, 75, or 80° C. for at least 0.5, 1.0, 1.5, 2.0, 2.5, 3.0, 3.5, or 4.0 hours. For example, in some embodiments, the slurry mixture is heated in a water bath to a temperature of 60° C. for 3 hours.

In further embodiments, the soaking periods comprise mixing the heated slurry mixture while being cooled to about 4° C. (e.g., 2-8° C.) for at least 12, 13, 14, 15, 16, 17, 18, 19, 20, 21, 22, 23, or 24 hours. For example, in some embodiments the heated slurry mixture is cooled to 4° C. for 16 hours. In further embodiments, the heated slurry mixture is mixed while being cooled for at least 18 hours, at least 20 hours, at least 22 hours, at least 24 hours, or at least 26 hours. In certain embodiments, the processing step comprises three or more heating periods and two or more soaking periods. For example, the processing step may comprise: (i) a first heating period comprising heating the slurry mixture to a temperature of 60° C. for 15 minutes; (ii) a first soaking period comprising mixing the heated slurry mixture while being cooled at 4° C. for at least 18 hours; (iii) a second heating period comprising heating the slurry mixture to a temperature of 60° C. for 15 minutes; (iv) a second soaking period comprising mixing the heated slurry mixture while being cooled at 4° C. for at least 18 hours; and (v) a third heating period comprising heating the slurry mixture to a temperature of 60° C. for 15 minutes. In some embodiments, the processed slurry mixture is at least partially homogenized.

Date palms can contain antimicrobial compounds that inhibit bacterial growth. It can be important to eliminate these compounds so that they are not present in culture media. Additionally, the high concentration of sugars in date palms can cause osmotic pressure that inhibits bacterial growth. In some embodiments, the method of preparing a DPE broth comprises separating the processed slurry mixture into DPE broth and DPF. The DPE broth may be separated from the slurry mixture by any means known in the art. For example, the processed slurry mixture may be filtered or decanted to leave out longer fibers and heavier particulate material to produce date palm extract broth. Filtration or decanting of the slurry mixture results in two products: (1) the DPE broth and (2) date palm fibers (DPFs). Any method of filtration generally known in the art may be used, including but not limited to cheesecloth, filter paper, filter membrane. In an embodiment, cheesecloth, or a similar material, may be used to filter the slurry mixture. Cheesecloth is available in a variety of grades, depending on the thread count per square inch, including grade 10, grade 40, grade 50, grade 60, grade 80, and grade 90. In an embodiment, grade 50 cheesecloth may be used. In some embodiments, the processed slurry mixture may be placed upon the filter. The filtrate may be passed through the filter into a collection vessel. The filtride is the substance that remains on the filter after the filtrate passes through it. In some embodiments, the filtrate is the DPE broth and the filtride is the DPF. Date palm fiber is a dietary fiber consisting mainly of polysaccharides (e.g., cellulose and pectin) and insoluble proteins. DPF is primarily composed of cellulose, hemicelluloses, pectin, and lignin.

In some embodiments, the extracted DPE broth or DPE broth with fibers may be sterilized. Any method of sterilization generally known in the art may be used. Typically, autoclaving can be used to perform sterilization. Autoclaves are able to sterilize by subjecting the components to be sterilized to high-pressure saturated steam. In some embodiments, DPE broth may be heated to a temperature for some amount of time capable of killing microorganisms with minimal damages to nutritional components of the media. Generally, short-duration, high temperature processes are more lethal to organisms, while causing less damage to nutrient components of media. In certain embodiments, the DPE broth may be autoclaved for at least 10 mins, at least 15 mins, at least 20 mins, at least 25 mins, or at least 30 mins. In some embodiments, the DPE broth is autoclaved at 10 psi, 11 psi, 12, psi, 13 psi, 14 psi, 15 psi, 16 psi, 17 psi, 18 psi, or 20 psi. In some embodiments, the DPM is autoclaved to a temperature of at least 100° C., 105° C., 110° C., 115° C., 120° C., or 125° C. In an embodiment, the DPE broth may be sterilized using the autoclave for 10-30 minutes at 106-120° C. In some embodiments DPM can be sterilized via passing thru a chamber preheated to a high temperature of at least 125 , 135, 140, 145,150, 155, 160, 165, 170 or 175° C. for a short period of time of at least 10, 15, 20, 25, or 30 seconds.

The DPE broth comprises a variety of nutritive components that can support growth of bacteria and other microorganisms. Carbohydrates, such as soluble sugars, are the predominant components in date fruit, which also contain lipids, proteins, and ash. In some embodiments, the DPE broth comprises calcium, iron, magnesium, manganese, sodium, fructose, glucose, lactose, maltose, and sucrose. As noted above, date palms are also a rich source of carbohydrates (mainly starch and sugars), some amino acids, vitamins (vitamin A, vitamin C, thiamin (B1), riboflavin (B2), niacin, and vitamin E), minerals (calcium, iron, magnesium, phosphorus, potassium, sodium, and zinc), dietary fiber and also contain other minor nutrients such as antioxidants, triglycerides, linoleic acid, and palmitic acid.

In some instances, the provided methods produce a DPE broth comprising calcium in the range of 5 to 20 mg calcium/100 g DPE solution. In an embodiment, the provided methods produce DPE solution comprising 11.5 mg calcium/100 g DPE solution. In some instances, the provided methods produce DPE solution comprising <0.1 mg iron/100 g DPE solution. In some instances, the provided methods produce DPE solution comprising magnesium in the range of 5 to 20 mg magnesium/100 g DPE solution. In an embodiment, the provided methods produce DPE solution comprising 11.5 mg magnesium/100 g DPE solution. In some instances, the provided methods produce DPE solution comprising sodium in the range of 2 to 15 mg sodium/100 g DPE solution. In an embodiment, the provided methods produce DPE solution comprising 6.48 mg sodium/100 g DPE solution.

Dates consist of a mixture of sucrose, glucose, and fructose. Early in development, dates have relatively high sucrose content. However, as dates develop, sucrose is inverted into glucose and fructose by the enzyme invertase. In some embodiments, dates used for the preparation of DPE contain mainly invert, monosaccharide sugars (fructose and glucose). In some instances, the provided methods produce DPE solution comprising at least 5% fructose. In some instances, the provided methods produce DPE comprising at least 5%, 6%, 7%, or 8% fructose. In an embodiment, the provided methods produce DPE comprising 6.98% fructose. In some instances, the provided methods produce DPE solution comprising at least 5% glucose. In some instances, the provided methods produce DPE comprising at least 5%, 6%, 7%, 8%, 9%, or 10% glucose. In an embodiment, the provided methods produce DPE comprising 7.39% glucose.

Dates typically contain small amounts of disaccharides (lactose, maltose, and sucrose). As dates develop, the sucrose content decreases as the sucrose is inverted into monosaccharide sugars (fructose and glucose). In some instances, the provided methods produce DPE solution comprising <0.05% maltose, <0.05% lactose and/or <0.05% sucrose. In some embodiments, the total sugar content is <25%, <20%, <15%, or <10%. For example, in one embodiment, DPE broth comprises about 14.37% total sugar content.

Method for Preparing Date Palm Medium and Date Palm Medium with Fiber

In another aspect, provided is a method of preparing a date palm medium (DPM) for cultivating microorganisms comprising: (i) preparing a buffer solution, (ii) buffering a date palm extract (DPE) broth with the buffer solution, wherein the DPE is prepared according to the methods described herein, and (iii) adding a nitrogen source of non-animal origin to the buffered DPE broth. In yet another aspect, provided is a method of preparing a date palm medium with fiber (DPFM) for cultivating microorganisms comprising: (i) preparing a buffer solution, (ii) buffering a date palm extract (DPE) broth with the buffer solution, wherein the DPE is prepared according to the methods described herein, (iii) adding an amount of date palm fiber (DPF), wherein the DPF is isolated according to the method described herein, and (iv) adding a nitrogen source of non-animal origin to the buffered DPE broth In yet another aspect, provided is a method of preparing a date palm medium with fiber (DPFM) for cultivating microorganisms comprising: (i) preparing a buffer solution, (ii) buffering a date palm extract broth with fibers (DPEF) with the buffer solution, wherein the DPEF is prepared according to the methods described herein, and (iii) adding a nitrogen source of non-animal origin to the buffered DPEF.

In some embodiments, date palm fiber (DPF) is added to the DPM to create DPM with fiber (DPFM). Some bacteria (e.g., *Lactobacillus* spp.) are fastidious microorganisms, and depend on extrinsic factors for growth, a specific pH, and fermentable nutrients for growth. Certain bacteria species have the ability to use fiber as a source of nutrients. In certain instances, DPFs are added to DPM prior to inoculation with bacteria.

In some embodiments, the method of preparing a DPM or DPFM for cultivating microorganisms comprises preparing a buffer solution. Any suitable buffer generally known in the art may be prepared. Suitable buffers include, but are not limited to, phosphate buffers, citrate buffers, lactate buffers, acetate buffers, carbonate buffers, Bis Tris, MES, and glycine-HCl. One or more surfactants may be added in combination to formulations of the buffer solution. Surfactants use may include, but are not limited to polyoxyethylene sorbitan alkyl esters, and/or Polysorbates 20, 21, 40, 60, 65, 80, 81, and 85. For example, the surfactant used may be TWEEN® 20 and/or 80. In certain embodiments, the concentration of the surfactant in the buffer solution may range from about 2.0-3.5% (v/v) depending on the bacterial strain used, from about 2.2-3.0% (v/v), or from about 2.3-2.5% (v/v).

Calcium chloride is an important growth factor for lactic acid bacteria, enhancing several enzymatic activities and aiding in cell division. In some embodiments, the concentration of calcium chloride in the buffer solution is at least 0.20 g/L, at least 0.25 g/L, or at least 0.30 g/L.

In some embodiments, the buffer solution may comprise L-Cysteine, HCl (1 g), disodium phosphate (2 g), ammonium citrate (2 g), sodium acetate (5 g), $MgSO_4 \cdot 7H_2O$ (0.1 g), and $MnSO_4 \cdot 5H_2O$ (0.05 g). The buffer solution may be prepared by combining 9.5 mM L-cysteine hydrochloride, 16.7 mM sodium phosphate, 8.2 mM ammonium citrate, 61 mM sodium acetate, 2.7 mM calcium chloride, 11.5 mM potassium phosphate, 1.7 mM magnesium sulfate, 0.3 mM manganese sulfate, 2.9 mM arginine and 30 mL of TWEEN®-80 to 1 L of deionized (DI) water. The pH of the buffer solution may range from about 5.5-6.2.

For example, in one embodiment, the method of preparing a DPM or DPFM for cultivating microorganisms comprises buffering a DPE broth. In certain embodiments, a DPE broth is buffered by adding a formulation of a buffer solution to the DPE broth. In some embodiments, the buffer solution is added to the DPE broth in a ratio of 1:4, 1:3, 1:2, 2:3, or 1:1 (buffer solution volume:DPE broth volume). In some embodiments, the buffer solution is added to the DPE solution in a volume to volume ratio of 2:3. The buffer solution may comprise, in some embodiments comprises L-cysteine hydrochloride, sodium phosphate, ammonium citrate, sodium acetate, calcium chloride, potassium phosphate, magnesium sulfate, manganese sulfate, arginine, Tween 80, and deionized water.

In some embodiments, the method of preparing a DPM or DPFM for cultivating microorganisms comprises adding a nitrogen source of non-animal origin to the buffered DPE broth. The nitrogen source in a medium for cultivating microorganisms is typically meat. However, animal products can be expensive and are difficult to procure. Thus, in some embodiments, peptones of non-animal origin are used as a source of nitrogen. Peptones are the product of the hydrolysis process of protein materials and are a source of nitrogen, carbon, minerals, and growth factors. The peptone composition may vary depending on the starting protein material, enzymes, and method for hydrolysis. The starting protein can be of animal or non-animal origin. Peptones of animal origin may include meat peptones (e.g., bactopeptone, beef extract, tryptose, and protease). Animal-free peptones may include soy peptones and yeast extracts. In some embodiments, the present invention utilizes peptones of non-animal origin as a nitrogen source. Alternatively, the nitrogen source may be any suitable source of nitrogen for culturing the bacteria of interest.

In some embodiments, the nitrogen source is a peptone, tryptone, proteose peptone, phytone peptone, polypeptone peptonetryptic soy broth, or yeast extract. Peptones are the hydrolyzed protein product from enzymatic or acidic digestion. For example, in some embodiments, the nitrogen source is Phytone™ peptone, a papiac digest of soybean meal with high vitamin and high carbohydrate content. In another embodiment, the nitrogen source is Yeast Extract, an autolysate of harvested yeast, *saccharomyces* spp.

Microorganisms typically require additional growth factors for cultivating in media, such as vitamins, amino acids, and fatty acids. Any additive suitable for cultivating the microorganism may be added to the DPM or DPFM. In some embodiments, the method of preparing a DPM for cultivating microorganisms comprises adding cysteine sulfide reducing agents to the DPM or DPFM. Suitable cysteine sulfide reducing agents may include sodium sulfide and L-cysteine hydrochloride and the hydrates thereof. In some embodiments, the method of preparing a DPM for cultivating microorganisms comprises adding Castenholz salts to the DPM or DPFM. Castenholz salts may include agar, sodium nitrate, sodium phosphate, potassium nitrate, nitrilotriacetic acid, magnesium sulfate heptahydrate, anhydrous calcium sulfate, sodium chloride, and/or manganese sulfate.

In some embodiments selective and/or differential components may be added to the DPM. Selective components are those that allow the growth of some microorganisms while inhibiting the growth of other microorganisms. Selective components may be added to inhibit the growth of non-target microorganisms. Differential components distinguish one microorganism type from another growing on the same media at the same time. Differential components may include pH indicators, which can be used to differentiate many microorganisms.

In some embodiments, methods for preparing DPM or DPFM comprise sterilization. For example, autoclaving can be used to sterilize media by killing microorganisms. In some embodiments, the DPM or DPFM is heated to a temperature for some amount of time capable of killing microorganisms with minimal damages to nutritional components of the media. In certain embodiments, the DPM or DPFM is autoclaved for at least 10 mins, at least 15 mins, at least 20 mins, at least 25 mins, or at least 30 mins. In some embodiments, the DPM or DPFM is autoclaved to a temperature of at least 105° C., 110° C., 115° C., 120° C., 125° C., or 130° C. For example, in some embodiments, the DPM or DPFM is autoclaved to a temperature between 120° C. and 121° C. In some embodiments, the DPM or DPFM is autoclaved at 10 psi, 11 psi, 12, psi, 13 psi, 14 psi, 15 psi, 16 psi, 17 psi, 18 psi, or 20 psi. In some embodiments, the DPM or DPFM is heated to 120 degrees for 15 mins. In some embodiments DPM or DPFM can be sterilized by passing the media through a chamber preheated to a temperature of at least 125, 130, 135, 140, 145, 150° C. or 175° C. for a short period of time of at least 10, 15, 20, 25, 30 seconds. Optimal heating time and temperature is dependent on volume of media being sterilized. In certain embodiments filtration may be used in combination with autoclaving to further sterilize the media or any other methods generally known in the art may be used to sterilize the DPM or DPFM is filtered.

In some embodiments, date palm fiber (DPF) is added to the DPM to create DPM with fiber (DPFM). In other embodiments, a slurry mixture of a high concentration of DPF in DPM (DPF slurry) is added to DPM to create DPFM. In certain instances, DPF or DPF slurry is added to DPM prior to inoculation with bacteria. In other instances, DPF or DPF slurry is added to DPM following inoculation with bacteria. DPF may be added at any time prior to or following inoculation with bacteria or other microorganisms of interest. In some embodiments, DPF or DPF slurry is added to DPM bacteria cultures 12 hour, 18 hours, 24 hours, 30 hours, 36 hours, or 48 hours following inoculation with bacteria. For example, LAB may be cultured in DPM. Following 24 hours of incubation, the pH may decrease from about 4.2-4.5. DPF may be added to the culture in order to increase the pH to a level that is suitable for LAB growth (e.g., pH 6-6.5). The addition of fiber to DPM cultures can help to reduce the rates of fermentation time and boost growth of bacteria (e.g., LAB). In some embodiments, the fiber added to the DPM may be fiber from a source other than dates. Any suitable fiber for providing fermentable nutrients and increasing pH may be used.

Date Palm Medium Composition

In another aspect, the invention provides a date palm medium (DPM) for cultivating microorganisms comprising (i) a buffered date palm extract (DPE) and (ii) a nitrogen source. In yet another aspect, the invention provides a date palm medium with date palm fiber (DPFM) for cultivating microorganisms comprising (i) a buffered date palm extract (DPE), (ii) an amount of date palm fiber (DPF) and (iii) a nitrogen source.

Different species of Lactobacillus have different nutritional requirements, and therefore, different media are required for growth of different species. Due to the high nutrient requirement for growing Lactobacillus species, growth media are costly to make and Lactobacillus species are difficult to grow in laboratory settings.

In some embodiments, the DPM comprises a buffered date palm extract. The buffered DPE may comprise any suitable buffer solution generally known in the art. Suitable buffer solutions include, but are not limited to, phosphate buffers, citrate buffers, lactate buffers, acetate buffers, carbonate buffers, Bis Tris, MES, and glycine-HCl. The buffer solution may comprise one or more surfactants. Suitable surfactants may include polyoxyethylene sorbitan alkyl esters, and/or Polysorbates 20, 21, 40, 60, 65, 80, 81, 85. For example, the surfactant may be TWEEN® 20 and/or 80. The concentrations of the surfactant in the buffer solution are typically in the range of 22-30% (v/v), preferably from about 23-25% (v/v). For example, the buffer solution may comprise Tween 80 (1 mL), L-Cysteine, HCL (1 g), disodium phosphate (2 g), ammonium citrate (2 g), sodium acetate (5 g), $MgSO_4.7H_2O$ (0.1 g), and $MnSO_4.5H_2O$ (0.05 g). In some embodiments, the buffer solution may be prepared by combining 9.5 mM L-cysteine hydrochloride, 16.7 mM sodium phosphate, 8.2 mM ammonium citrate, 61 mM sodium acetate, 2.7 mM calcium chloride, 11.5 mM potassium phosphate, 1.7 mM magnesium sulfate, 0.3 mM manganese sulfate, 2.9 mM arginine and 30 mL of TWEEN®-80 to 1 L of deionized (DI) water. The range of pH of the buffer solution is from 5.5-6.2.

In certain embodiments, the buffered DPE broth comprises buffer solution and DPE broth in a ratio of 1:4, 1:3, 1:2, 2:3, or 1:1 (buffer solution volume:DPE broth volume). For example, in one embodiment, the buffered DPE broth comprises buffer solution and DPE broth in a volume to volume ratio of 2:3. The DPE broth should be present in an amount that is suitable for growth of microorganisms (e.g., Lactobacillus spp. or Bifidobacterium spp.). In certain embodiments, the amount of DPE is 55 to 60 wt % based on a total weight of the date palm medium (DPM). In some embodiments, the DPM does not require an additional carbon source (e.g., fructose or lactose). In some embodiments, the DPM does not require any additional compounds (e.g., trace elements, antioxidants, minerals or vitamins). In alternative embodiments, the DPM may comprise additional vitamins beneficial for growth of the microorganism of interest (e.g., Lactobacillus spp. or Bifidobacterium spp.). Additionally, the DPM may comprise additional trace elements beneficial for growth of the microorganism of interest (e.g., $Cu^-$, $Zn^-$, $Mn^-$, $Mg^-$, $Co^-$, or any combinations thereof). In certain embodiments, the DPM may comprise an amount of DPF. DPFs may provide an additional source of nutrients and maintain an optimal pH for culturing microorganisms of interest.

As discussed in detail herein, the DPM for cultivating microorganisms may comprise a nitrogen source of non-animal origin. Thus the DPM may utilize peptones of non-animal origin as a nitrogen source. In some embodiments, the nitrogen source is a peptone, tryptone, proteose peptone, phytone peptone, Polypeptone peptonetryptic soy broth, or yeast extract. Peptones are the hydrolyzed protein product from enzymatic or acidic digestion. In some embodiments, the nitrogen source is Phytone™ peptone, a papiac digest of soybean meal with high vitamin and high carbohydrate content. Alternatively and/or additionally, peptones of animal origin may be used.

As discussed in detail herein, and depending on which microorganism is being cultured, additional growth factors may include, but are not limited to vitamins, amino acids, and fatty acids. The DPM may comprise any additive suitable for cultivating the microorganism of interest. In some embodiments, the DPM may further comprise selective and/or differential components. Selective components may be added to inhibit the growth of non-target microorganisms. Differential components may include pH indicators, which can be used to differentiate many microorganisms.

Methods of Cultivating Microorganisms Using Date Palm Medium

Typically, bacterial growth requires carbohydrates, amino acids, vitamins, and minerals. In another aspect, provided is a method of cultivating microorganisms comprising: (i) inoculation a date palm medium (DPM) with microorganisms of interest; (ii) incubating the microorganisms of interest under growth conditions such that growth occurs. In yet another aspect, provided is a method of cultivating microorganisms comprising: (i) inoculation a date palm medium with date palm fiber (DPFM) with microorganisms of interest; (ii) incubating the microorganisms of interest under growth conditions such that growth occurs.

In some embodiments, the method of cultivating microorganisms comprises inoculating a DPM or DPFM with microorganisms of interest. In some embodiments, the DPM or DPFM is inoculated with fastidious organisms. Fastidious organisms require specific nutrients for growth. For example, lactic acid bacteria (LAB), such as Lactobacillus spp., require amino acids, peptides, nucleic acid derivatives, vitamins, salts, fatty acid esters, and fermentable carbohydrates for growth.

A number of LAB have been identified for their use as probiotics, which are food supplements containing live microorganisms that have beneficial effects. LAB are found in the gastrointestinal tract and aid in digestion. A number of LAB species are used as probiotics, including L. acidophilus, L. rhamnosus, B. longus, and B. bifidum.

Some species of bacteria metabolize carbohydrates, including sugars (e.g. glucose, fructose, sucrose). For example, some species of Lactobacillus produce functional enzymes such as α-glucosidase, β-glucosidase, acid phosphatase, and phytase, and therefore, can have an important impact on human health. The enzyme α-glucosidase allows for the breakdown of starch and disaccharides into sugar, while β-glucosidase catalyzes the hydrolysis of glycosidic bonds to terminal non-reducing residues in beta-D glucosides and oligosaccharides with release of glucose. Acid phosphatase frees attached phosphoryl groups from other molecules during digestion and phytase catalyzes the hydrolysis of phytic acid, an indigestible, organic form of phosphorous that is found in grains and oil seeds, and releases a usable form of inorganic phosphorous.

In some instances, the disclosed methods are used to cultivate Gram-positive or Gram-negative bacteria or combinations thereof. In certain embodiments, DPM or DPFM is used to cultivate lactic acid bacteria. In some embodiments, DPM or DPFM is used to cultivate a lactobacillus species. In another aspect, the present invention provides a method for growing a probiotic strain of Lactobacilli. A number of lactobacillus strains are useful as probiotics including L. casei, L. acidophilus, L. fermentum, L. plantarum, L. lactis, and L. reuteri. Or the DPM or DPFM may be used to culture other bacteria such as, but not limited to L. rhamnosus, L. reuteri, B. bifidum, B. animalis, and B. longus.

In some embodiments, the methods of cultivating microorganisms comprises using DPM or DPFM. In some embodiments, DPM comprises (i) a buffered date palm extract (DPE) and (ii) a nitrogen source. In other embodiments, DPFM comprises (i) a buffered date palm extract (DPE), (ii) an amount of DPF, and (iii) a nitrogen source. In some embodiments, the DPM or DPFM is used to cultivate fastidious bacteria including, but not limited to *L. rhamnosus, L. reuteri, B. bifidum, B. animalis,* and *B. longus.* In certain embodiments, DPM is inoculated with at least 0.5%, 1.0%, 1.5%, 2.0%, 2.5%, 3%, 3.5%, 4.0%, 4.5%, 5.0% bacteria by volume. In some embodiments, DPM or DPFM is inoculated with 1-2% bacteria by volume.

In some embodiments, date palm fiber (DPF) is added to the DPM to create DPM with fiber (DPFM). In certain instances, DPF is added to DPM prior to inoculation with bacteria. In other instances, DPF is added to DPM following inoculation with bacteria. DPF may be added at any time prior to or following inoculation with bacteria or other microorganisms of interest. In some embodiments, the fiber is added to DPM bacteria cultures 12 hour, 18 hours, 24 hours, 30 hours, 36 hours, or 48 hours following inoculation with bacteria. For example, LAB may be cultured in DPM. Following 24 hours of incubation, the pH may decrease from about 4.2-4.5. DPF may be added to the culture in order to increase the pH, to a level that is suitable for LAB growth (e.g., pH 6-6.5). The addition of fiber to DPM cultures can help to reduce the rates of fermentation time and boost growth of bacteria (e.g., LAB). In some embodiments, the fiber added to the DPM may be fiber from a source other than dates. Any suitable fiber for providing fermentable nutrients and increasing pH may be used.

Conditions such as temperature, pH, oxygen and growth media nutritional content can affect bacteria growth activity. In some embodiments, bacteria are grown in anaerobic environments. pH ranges desirable for bacterial growth varies by species. In some embodiments, the pH ranges from 4 to 9 depending on the species of bacteria being cultivated. For example, a pH of 5.5 is optimal for cultivating *Lactobacillus* spp. In some embodiments, bacteria are cultivated under anaerobic conditions. In other embodiments, bacteria are cultivated under microaerophilic conditions. Microaerophilic conditions provide oxygen, but at levels lower than those present in the atmosphere.

Probiotics Cultivated in DPM or DPFM

Another aspect of the invention relates to a probiotic comprising bacteria cultivated in DPM or DPFM. As discussed in detail herein, the DPM used to cultivate the probiotic comprises a buffered DPE and a nitrogen source. Alternatively, DPFM used to cultivate the probiotic comprises a buffered DPE, and an amount of added or retained DPF, and a nitrogen source. Probiotics may be useful in reestablishing beneficial bacteria in the intestinal tract. Probiotics may consist of beneficial bacteria that are helpful in digesting food and nutrient absorption. In some instances the cultivated bacteria may be used to make a probiotic. In some embodiments, the probiotic may be a dietary supplement. In some embodiments, probiotic strains may be heat-dried or freeze-dried. For example, the bacteria cultivated in DPM or DPFM may be freeze-dried and formulated in a capsule, powder, sachet, or tablet form. The particular form of the probiotic is not essential to this invention. In other embodiments, the probiotic and media may be incorporated into a liquid formulation.

In other embodiments, the probiotic comprising bacteria cultivated in DPM or DPFM may be a food supplement. In certain instances, the probiotic cultures used to supplement food may be live bacteria. Bacteria cultivated in DPM or DPFM may be added to a variety of food types (e.g., yogurt, milk, cheese, juice, ice cream, cereal, bread, or noodles) or feed. Any suitable food product may be supplemented with a probiotic.

Any microorganism that when administered in adequate amounts, confers a health benefit on the host and that can be cultivated in DPM or DPFM, may be used as a probiotic in accordance with an embodiment of the present disclosure. LAB can be used to process foodstuffs and preserve food by inhibiting the growth of other microorganisms. Both *Bifidobacterium* and *Lactobacillus* ferment carbohydrates and produce lactic acid, and therefore, aid in digestion and nutrient absorption. In some embodiments, the probiotic comprises at least one of a *Lactobacillus* species or a *Bifidobacterium* species.

EXAMPLES

The following examples describe methods for the preparation and use of date palm medium (DPM) and demonstrate the ability to cultivate bacteria using media comprising animal-free components.

Materials

The following materials were used in the examples and methods below:

1. Lactobacilli MRS Broth—Neogen, 1619 E Kalamazoo St, Lansing, Mich. 48912
2. Khalas Dates—Al Qasseim Private Date Palm Farm, Saudi Arabia
3. Bacterial strains used and sources are listed in the table below (Table I)

TABLE I

Bacterial strains used and their short forms and sources.

| Bacterial Strain | Source |
| --- | --- |
| *Lactobacillus rhamonus* (LGG) | Food Microbiology Laboratory, NC A&T University, 1601 E Market St, Greensboro, NC 27401 |
| *Lactobacillus reuteri* (LD SM) DSM 20016 | Food Microbiology Laboratory, NC A&T University, 1601 E Market St, Greensboro, NC 27401 |
| *Lactobacillus reuteri* SD 2112 | Food Microbiology Laboratory, NC A&T University, 1601 E Market St, Greensboro, NC 27401 |
| *Bifidobacterium bifidum* (B1) ATCC 15696 | Food Microbiology Laboratory, NC A&T University, 1601 E Market St, Greensboro, NC 27401 |
| *Bifidobacterium bifidum* (B2) ATCC 35914 | Food Microbiology Laboratory, NC A&T University, 1601 E Market St, Greensboro, NC 27401 |
| *Bifidobacterium animalis* (B3) Bb12 | Food Microbiology Laboratory, NC A&T University, 1601 E Market St, Greensboro, NC 27401 |
| *Bifidobacterium longum* (B4) ATCC 15707 | Food Microbiology Laboratory, NC A&T University, 1601 E Market St, Greensboro, NC 27401 |
| *Lactobacillus rhamnosus* (1347) NCIMB10463 | Nizo, Ede, Netherlands |
| *Lactobacillus plantarum* (WCFSI) Nizo 1836 | Nizo, Ede, Netherlands |
| *Bifidobacterium longum* (NIZO 404) ATCC 27920 | Nizo, Ede, Netherlands |
| *Lactobacillus plantarum* (NIZO 2834) | Nizo, Ede, Netherlands |
| *Lactobacillus rhamnosus* (LGG) Nizo 3442 | Nizo, Ede, Netherlands |

Example 1

Extraction of Broth from Date Palms

Sealed, organic khalas dates (Al Qasseim Private Date Farm, Saudi Arabia) were removed from their packaging, weighed, and pressed using a mechanical press for 4 days allowing the liquid to be released from the dates at room temperature. After day 4, the press was released, and the seeds were removed from the date presscake. The date presscake was weighed and a 220 g sample of date presscake was mixed with 500 mL of de-ionized (DI) water i.e., a 1:2.27 (date presscake:water m/v ratio) resulting in slurry. The slurry was heated using a water bath to 60° C. for 15 minutes. The heated slurry mixture was then mixed for 1 hour using a magnetic stirrer, followed by refrigeration for 24 hours. After 24 hours, the slurry was heated for a second time using a water bath to 60° C. for 15 minutes. The re-heated slurry mixture was then filtered through cheese cloth to obtain a broth of date palm extract (DPE) and a filtride of date palm fiber (DPF). The broth was then sterilized using the autoclave for 15 minutes at 120° C.

TABLE II

Khalas Date Nutritional Composition Pre- and Post-Pressing
KHALAS DATE COMPOSITION

| Ingredients | Pressed Type (s) | Extracted Type (l) |
|---|---|---|
| Calcium | 36.2 mg/100 g | 11.5 mg/100 g |
| Iron | 1.27 mg/100 g | <0.1 mg/100 g |
| Magnesium | 45.6 mg/100 g | 11.5 mg/100 g |
| Manganese | 0.24 mg/100 g | 0.05 mg/100 g |
| Sodium | 2.25 mg/100 g | 6.48 mg/100 g |
| Fructose | 28.60% | 6.98% |
| Glucose | 30.57% | 7.39% |
| Maltose | <0.05% | <0.05% |
| Sucrose | <0.05% | <0.05% |
| Total Sugar | 59.17% | 14.37% |

Example 2

Preparation of Date Palm Medium

A buffer solution of 1 liter was prepared which contains 9.5 mM L-cysteine hydrochloride, 16.7 mM sodium phosphate, 8.2 mM ammonium citrate, 61 mM sodium acetate, 2.7 mM calcium chloride, 11.5 mM potassium phosphate, 1.7 mM magnesium sulfate, 0.3 mM manganese sulfate, 2.9 mM arginine and 3% of TWEEN®-80. The developed medium was comprised of the DPE broth and the buffer solution described above in a 2:3 (buffer:DPE) ratio followed by the addition of phytone peptone (the nitrogen source of the medium) in a 2:25 (phytone peptone:buffer+DPE) v/v ratio.

Example 3

Bacterial Growth Comparison of MRS and DPM by Determination of Cell Mass

The previously prepared date palm medium was inoculated with bacteria (1.4% by volume) obtained from a three-fold dilution of overnight active culture grown in MRS into 9 mL peptone water, while an MRS broth sample of equal volume was also inoculated with the same amount of bacteria and used as the control. After inoculation, 1 mL was removed from each sample to perform a two-fold dilution into 9 mL peptone water followed by plating a 100 μL sample from the dilutions onto MRS agar plates (0 hr time point). The plates, as well as the original samples, were then incubated overnight at 37° C. The next day, samples were removed from the incubator, and 1 mL was removed from each sample to perform a seven-fold dilution into 9 mL peptone water followed by plating a 100 μL sample from the sixth and seventh dilutions onto MRS agar plates (24 hr time point). The plates were then incubated overnight at 37° C. Bacterial cell mass was determined at inoculation and 24 hours post inoculation per sample grown on MRS agar plates, and the results were expressed as log colony forming units (CFU)/mL.

Example 4

Date Palm Fiber Medium Preparation and Determination of Cell Mass

The effects of adding date palm fibers to previously inoculated medium were evaluated to determine a) bacterial population present at the time of the fiber addition for each sample and b) bacterial population present 24 hours after the addition of fibers using MRS agar plates to grow and count the bacterial colonies and calculate log CFU/mL for each of the samples. The results were compared to determine which sample resulted in a superior cell mass.

The date palm fiber medium was prepared by adding the previously prepared buffer solution (BS) to the date palm fibers (DPF) in a 2:3 mL v/v ratio (BS to DPF respectively) followed by mixing using a vortex. Phytone peptone (8% by volume) was added to the BS-DPF mixture to complete the date palm medium+Fiber (DPFM). An equivalent amount of DPFM was then added to each of the previously inoculated samples from the 24 hr time point and to the previously inoculated MRS broth control sample from the 24 hr time point. Ten-fold serial dilutions were performed, A 1 mL sample was then removed from each sample to perform a six-fold dilution in 9 mL of peptone water followed by plating a 100 μL sample from the fifth and sixth dilutions onto MRS agar plates (0 hr time point for samples mixed with fiber). After 24 hours, samples were removed from the incubator, and 1 mL was removed from each sample to perform an eight-fold dilution in 9 mL of peptone water followed by plating a 100 μL sample from the sixth, seventh, and eighth dilutions onto MRS agar plates (24 hr time point for samples mixed with fiber). The plates were then incubated overnight at 37° C. FIG. 1 shows the percent growth after 24 hours of incubation. It can be seen that the growth of the various strains of bacteria was essentially equivalent in DPM as compared to MRS after 24 hours (FIG. 1, Table 3 and Table 4). Table 3 shows the raw data from these experiments. The addition of DPF to DPM to 24 hour cultures showed beneficial effects on growth of 5 of the 7 strains tested: *Lactobacillus rhamnosus* (LGG), *Lactobacillus reuteri* DSM (LDSM), *Lactobacillus reuteri* SD (LSD), *Bifidobacterium bifidum* (B1), *Bifidobacterium bifidum* (B2), *Bifidobacterium animalis* (B3), and *Bifidobacterium longum* (B4). Tables 4.1 and 4.2 and FIG. 1 show the mean data obtained.

TABLE 3

Bacterial Growth (log CFU/mL) After 24 Hour Incubation

| | | MRS | | | DPM | | | MRS + Fiber | | | DPM + Fiber | | |
|---|---|---|---|---|---|---|---|---|---|---|---|---|---|
| Timepoint | Strain | n | Mean | SD | n | Mean | SD | N | Mean | SD | n | Mean | SD |
| 0 Hour Incubation | LGG | 3 | 4.49 | 0.07 | 3 | 4.54 | 0.05 | 3 | 9.47 | 0.03 | 3 | 7.57 | 0.05 |
| | LDSM | 3 | 4.46 | 0.03 | 3 | 4.39 | 0.08 | 3 | 9.2 | 0.04 | 3 | 9.07 | 0.06 |
| | LSD | 3 | 4.35 | 0.14 | 3 | 4.32 | 0.18 | 3 | 9.59 | 0.05 | 3 | 9.02 | 0.05 |
| | B1 | 3 | 5.64 | 0.03 | 3 | 5.67 | 0.05 | 3 | 9.75 | 0.03 | 3 | 9.81 | 0.04 |

TABLE 3-continued

Bacterial Growth (log CFU/mL) After 24 Hour Incubation

| | | MRS | | | DPM | | | MRS + Fiber | | | DPM + Fiber | | |
|---|---|---|---|---|---|---|---|---|---|---|---|---|---|
| Timepoint | Strain | n | Mean | SD | n | Mean | SD | N | Mean | SD | n | Mean | SD |
| | B2 | 3 | 4.59 | 0.09 | 3 | 4.6 | 0.13 | 3 | 9.28 | 0.03 | 3 | 9.17 | 0.11 |
| | B3 | 3 | 4.59 | 0.05 | 3 | 4.78 | 0.07 | 3 | 9.49 | 0.01 | 3 | 9.12 | 0.05 |
| | B4 | 3 | 5.67 | 0.03 | 3 | 5.69 | 0.02 | 3 | 9.86 | 0.02 | 3 | 9.44 | 0.05 |
| 24 Hour | LGG | 3 | 9.19 | 0.02 | 3 | 8.28 | 0.09 | 3 | 8.89 | 0.1 | 3 | 9.63 | 0.1 |
| Incubation | LDSM | 3 | 9.98 | 0.1 | 3 | 10.86 | 0.02 | 3 | 8.85 | 0.04 | 3 | 9.21 | 0.02 |
| | LSD | 3 | 9.32 | 0.03 | 3 | 8.80 | 0.05 | 3 | 9.83 | 0.04 | 3 | 8.51 | 0.11 |
| | B1 | 3 | 10.28 | 0.05 | 3 | 10.37 | 0.03 | 3 | 9.84 | 0.03 | 3 | 10.79 | 0.07 |
| | B2 | 3 | 10.01 | 0.03 | 3 | 9.86 | 0.2 | 3 | 9.89 | 0.03 | 3 | 10.04 | 0.05 |
| | B3 | 3 | 10.4 | 0.07 | 3 | 9.64 | 0.05 | 3 | 9.96 | 0.05 | 3 | 10.33 | 0.03 |
| | B4 | 3 | 10.6 | 0.03 | 3 | 9.96 | 0.03 | 3 | 11.69 | 0.02 | 3 | 10.88 | 0.08 |

TABLE 4.1

DPM and MRS Bacterial Growth (% Growth (log CFU/mL) After 24 Hour Incubation Compared to 0 Hour Incubation)

| | | MRS | DPM |
|---|---|---|---|
| % Growth | LGG | 105% | 82% |
| | LDSM | 124% | 147% |
| | LSD | 114% | 104% |
| | B1 | 82% | 83% |
| | B2 | 118% | 114% |
| | B3 | 127% | 102% |
| | B4 | 87% | 75% |

TABLE 4.2

DPM and MRS Bacterial Growth (% Growth (log CFU/mL) After 48 Hour Total Incubation with Fiber added after 24 Hours Compared to 0 Hour Incubation)

| | | MRS + Fiber | DPM + Fiber |
|---|---|---|---|
| % Growth | LGG | 98% | 112% |
| | LDSM | 98% | 110% |
| | LSD | 126% | 97% |
| | B1 | 74% | 90% |
| | B2 | 115% | 118% |
| | B3 | 117% | 116% |
| | B4 | 106% | 91% |

Example 5

Demonstration of Enzymatic Functionality of Bacteria Cultures in DPM and DPFM

The superior enzymatic activity of bacteria cultured in the developed DPM and DFMF compared to commercial MRS was demonstrated by measuring the product of the enzymatic reaction as indicated by the ultraviolet absorbance of each sample before and after the addition of an appropriate substrate. The absorbance values were then used to calculate the enzyme units of each sample to identify the difference in levels of para-nitrophenol released by each enzyme.

A. α and β-Glucosidase Enzyme Activity of Cultured Bacteria

Un-inoculated MRS, DPM, MRS mixed with fibers, and DPFM were all dispensed separately into test tubes (1 mL each) followed by the addition of 4-nitrophenyl-α-D-glucopyranoside (2 mL, 10 mM) to each tube. Uninoculated MRS, DPM, MRS mixed with fibers, and DPFM were all dispensed separately into test tubes (1 mL each) followed by the addition of ρ-nitrophenyl-β-D-glucopyranoside (2 mL, 10 mM) to each tube. Overnight inoculated MRS, DPM, MRS mixed with fibers, and DPFM were all dispensed separately into test tubes (1 mL each) followed by the addition of 4-nitrophenyl-α-D-glucopyranoside (2 mL, 10 mM) to each tube. Overnight inoculated MRS, DPM, MRS mixed with fibers, and DPFM were all dispensed separately into test tubes (1 mL each) followed by the addition of ρ-nitrophenyl-β-D-glucopyranoside (2 mL, 10 mM) to each tube. All samples were labeled appropriately and incubated for 20 min at 37° C. After 20 min, sodium carbonate (5 mL, 0.5 M) was added to each sample to stop the reaction. Results (Table 4) were obtained using a Spectronic 21 to record absorbance values at 610 nm wavelengths before and after the addition of the substrate.

B. Acid Phosphatase Enzyme Activity of Cultured Bacteria

Un-inoculated MRS, DPM, MRS mixed with fibers, and DPFM were all dispensed separately into test tubes (1 mL each) followed by the addition of a sodium acetate buffer (1 mL, 0.1 M) containing 5 mM 4-nitrophenyl phosphate di(tris) salt to each tube. Overnight inoculated MRS, DPM, MRS mixed with fibers, and DPFM were all dispensed separately into test tubes (1 mL each) followed by the addition of a sodium acetate buffer (1 mL, 0.1 M) containing 5 mM 4-nitrophenyl phosphate di(tris) salt to each tube. All samples were labeled appropriately and incubated for 30 min in a water bath at 50° C. After 30 min, sodium hydroxide (2 mL, 1 M) was added to each sample to stop the reaction. Results (Table 4) were obtained using a Spectronic 21 to record absorbance values at 610 nm wavelengths before and after the addition of the substrate.

C. Phytase Enzyme Activity of Cultured Bacteria

Un-inoculated MRS, DPM, MRS mixed with fibers, and DPFM were all dispensed separately into test tubes (1 mL each) followed by the addition of a sodium acetate buffer (1.6 mL, 0.1 M) containing 1.2 mM sodium phytate to each tube. Overnight inoculated MRS, DPM, MRS mixed with fibers, and DPFM were all dispensed separately into test tubes (1 mL each) followed by the addition of a sodium acetate buffer (1.6 mL, 0.1 M) containing 1.2 mM sodium phytate to each tube. All samples were incubated for 30 min in a water bath at 50° C. After 30 min, trichloroacetic acid (0.6 mL, 20%) was added to each sample to stop the reaction. Results (Table 5) were obtained using a Spectronic 21 to record absorbance values at 610 nm wavelengths before and after the addition of the substrate.

TABLE 5

Enzyme Activity (Absorbance read at 610 nm and n = 3 for all samples)

| Bacteria | Enzyme Tested | MRS Mean Enzyme Units ± SD | DPM Mean Enzyme Units ± SD | MRS Fiber Mean Enzyme Units ± SD | DPM Fiber Mean Enzyme Units ± SD |
|---|---|---|---|---|---|
| LGG | α-Glucosidase | 46.22 ± 0.77 | 12 ± 2 | 53.03 ± 2.62 | 14.17 ± 0.72 |
|  | β-Glucosidase | 46.44 ± 0.38 | 14 ± 2.65 | 53.03 ± 2.62 | 13.75 ± 0 |
|  | Acid Phosphatase | 43.33 ± 3.33 | 28.33 ± 2.89 | 57.58 ± 5.25 | 58.33 ± 7.22 |
|  | Phytase | 66.67 ± 0 | 80.33 ± 0.58 | 90.91 ± 0 | 100 ± 0 |
| LDSM | α-Glucosidase | 40 ± 0 | 50 ± 0 | 42.42 ± 2.62 | 62.5 ± 0 |
|  | β-Glucosidase | 39.78 ± 0.38 | 57.14 ± 0 | 42.42 ± 2.62 | 62.92 ± 0.72 |
|  | Acid Phosphatase | 33.33 ± 3.33 | 20.24 ± 2.06 | 54.55 ± 0 | 50 ± 0 |
|  | Phytase | 66.67 ± 0 | 66.43 ± 1.89 | 90.91 ± 0 | 112.5 ± 0 |
| LSD | α-Glucosidase | 45.11 ± 0.38 | 48.61 ± 0.48 | 54.55 ± 0 | 91.43 ± 1.43 |
|  | β-Glucosidase | 45.33 ± 0 | 48.33 ± 0 | 54.55 ± 0 | 72.38 ± 1.65 |
|  | Acid Phosphatase | 33.33 ± 0 | 33.33 ± 0 | 45.45 ± 0 | 42.86 ± 0 |
|  | Phytase | 62.22 ± 3.85 | 69.44 ± 9.62 | 90.91 ± 0 | 114.29 ± 0 |
| B1 | α-Glucosidase | 8.44 ± 0.38 | 6.67 ± 0.72 | 40.91 ± 0 | 37.5 ± 0 |
|  | β-Glucosidase | 8.44 ± 0.38 | 6.67 ± 0.72 | 40.91 ± 0 | 38.33 ± 1.44 |
|  | Acid Phosphatase | 55.56 ± 3.85 | 41.67 ± 3.61 | 54.55 ± 0 | 56.25 ± 0 |
|  | Phytase | 73.33 ± 11.55 | 75 ± 0 | 81.82 ± 0 | 87.5 ± 0 |
| B2 | α-Glucosidase | 66.67 ± 0 | 87.5 ± 1.25 | 74.24 ± 2.62 | 78.15 ± 0.64 |
|  | β-Glucosidase | 66.67 ± 0 | 88.75 ± 1.25 | 72.73 ± 0 | 77.78 ± 0 |
|  | Acid Phosphatase | 57.78 ± 1.92 | 43.75 ± 0 | 59.7 ± 1.05 | 50 ± 0 |
|  | Phytase | 71.11 ± 3.85 | 79.17 ± 3.61 | 81.82 ± 0 | 100 ± 0 |
| B3 | α-Glucosidase | 26.89 ± 0.38 | 5.67 ± 0.58 | 58.89 ± 0.48 | 40 ± 1.11 |
|  | β-Glucosidase | 26.67 ± 0 | 5.67 ± 0.58 | 58.61 ± 0.48 | 40.74 ± 0.64 |
|  | Acid Phosphatase | 53.33 ± 0 | 35 ± 0 | 50 ± 0 | 50 ± 0 |
|  | Phytase | 68.89 ± 3.85 | 66 ± 6.93 | 68.06 ± 2.41 | 111.11 ± 0 |
| B4 | α-Glucosidase | 10 ± 0 | 7.08 ± 0.72 | 56.67 ± 0.52 | 44.17 ± 0.72 |
|  | β-Glucosidase | 10 ± 0 | 7.08 ± 0.72 | 57.27 ± 0.91 | 43.75 ± 0 |
|  | Acid Phosphatase | 53.33 ± 0 | 43.75 ± 0 | 55.45 ± 1.57 | 56.25 ± 0 |
|  | Phytase | 68.89 ± 3.85 | 79.17 ± 7.22 | 90.91 ± 0 | 125 ± 0 |

Example 6

Demonstration of Bacterial Freeze-Dry and pH Stability of Microbes Cultured in DPM and DPFM Three 200 mL batches of each sample (MRS, DPM, and DPFM) were poured into multiple appropriately labeled plates containing 6 mL each and then freeze dried. Two of each sample type was sub-inoculated into 10 mL of MRS followed by incubation at 37° C. while undergoing shaking for 20 minutes. After 20 minutes, the samples were removed and exposed to a pH of 2 and a pH of 6.5 separately and simultaneously. The samples were then serially diluted (10 fold) four times followed by cell mass determination at 0 time and 120 minutes after exposure by surface plating. The rest of the freeze dried samples were separated into two groups: the first group was stored at room temperature while the other group was stored at 4° C. After 2 weeks, and 1 month, cell mass was determined for each group of freeze dried samples to demonstrate viability with respect to time and temperature.

TABLE 6

Effect of pH and temperature on Stability of Lactobacillus and Bifidostrains during Storage at Room Temperature and 4° C.

| Bacteria | Media | 0 Hour pH 6.5 Log CFU ± SD | 0 Hour pH 2 Log CFU ± SD | 2 Hour pH 6.5 Log CFU ± SD | 2 Hour pH 2 Log CFU ± SD | 2 Weeks RT Log CFU ± SD | 2 Weeks 4° C. Log cFu ± SD | 1 Month RT Log CFU ± SD | 1 Month 4° C. Log CFU ± SD |
|---|---|---|---|---|---|---|---|---|---|
| LGG | MRS | 8.76 ± 0.02 | 8.48 ± 0.04 | 8.93 ± 0.05 | 7.60 ± 0.08 | 5.66 ± 0.32 | 7.23 ± 0.04 | 2.14 ± 0.05 | 8.20 ± 0.13 |
|  | DPM | 9.61 ± 0.02 | 9.47 ± 0.02 | 9.71 ± 0.01 | 9.16 ± 0.03 | 5.77 ± 0.27 | 8.93 ± 0.05 | 3.37 ± 0.21 | 8.57 ± 0.05 |
|  | DPFM | 9.64 ± 0.04 | 9.59 ± 0.01 | 9.85 ± 0.01 | 9.11 ± 0.06 | 6.01 ± 0.17 | 8.78 ± 0.09 | 3.87 ± 0.05 | 8.60 ± 0.05 |
| LDSM | MRS | 7.80 ± 0.04 | 8.02 ± 0.03 | 8.29 ± 0.01 | 7.24 ± 0.11 | 5.700 ± 0.00 | 7.51 ± 0.10 | 3.50 ± 0.07 | 6.51 ± 0.04 |
|  | DPM | 8.47 ± 0.01 | 8.27 ± 0.02 | 8.87 ± 0.03 | 7.62 ± 0.03 | 6.50 ± 0.07 | 8.14 ± 0.02 | 4.30 ± 0.6 | 7.1 ± 0.00 |
|  | DPFM | 8.47 ± 0.04 | 8.41 ± 0.06 | 8.99 ± 0.02 | 7.74 ± 0.05 | 6.9 ± 0.05 | 7.72 ± 0.07 | 5.01 ± 0.15 | 6.88 ± 0.10 |
| ATCC | MRS | 7.93 ± 0.05 | 8.22 ± 0.03 | 8.46 ± 0.02 | 7.47 ± 0.09 | 6.30 ± 0.30 | 7.38 ± 0.06 | 3.89 ± 0.06 | 6.88 ± 0.06 |
|  | DPM | 9.03 ± 0.02 | 8.57 ± 0.02 | 9.34 ± 0.03 | 7.89 ± 0.03 | 6.22 ± 0.21 | 8.68 ± 0.04 | 3.95 ± 0.13 | 7.98 ± 0.02 |
|  | DPFM | 9.11 ± 0.03 | 8.66 ± 0.06 | 9.42 ± 0.02 | 8.02 ± 0.05 | 8.68 ± 0.04 | 7.45 ± 0.05 | 4.87 ± 0.05 | 6.95 ± 0.02 |
| B1 | MRS | 7.93 ± 0.05 | 8.22 ± 0.03 | 8.46 ± 0.02 | 7.47 ± 0.09 | 7.00 ± 0.61 | 7.38 ± 0.06 | 3.92 ± 0.02 | 6 ± 0.04 |
|  | DPM | 9.03 ± 0.02 | 8.57 ± 0.02 | 9.34 ± 0.03 | 7.89 ± 0.03 | 7.60 ± 0.11 | 8.68 ± 0.04 | 4.09 ± 0.05 | 7.41 ± 0.04 |
|  | DPFM | 9.11 ± 0.03 | 8.66 ± 0.06 | 9.42 ± 0.02 | 8.02 ± 0.05 | 7.87 ± 0.03 | 7.45 ± 0.05 | 4.76 ± 0.04 | 7.5 ± 0.04 |

TABLE 6-continued

Effect of pH and temperature on Stability of Lactobacillus and Bifidostrains during Storage at Room Temperature and 4° C.

| | | Time Point: | | | | | | | |
|---|---|---|---|---|---|---|---|---|---|
| | | 0 Hour | | 2 Hour | | 2 Weeks | | 1 Month | |
| | | pH/Storage: | | | | | | | |
| | | pH 6.5 | pH 2 | pH 6.5 | pH 2 | RT | 4° C. | RT | 4° C. |
| | | Log | Log | Log | Log | Log | Log | Log | Log |
| | | CFU ± | CFU ± | CFU ± | CFU ± | CFU ± | cFu ± | CFU ± | CFU ± |
| Bacteria | Media | SD | SD | SD | SD | SD | SD | SD | SD |
| B2 | MRS | 10.16 ± 0.02 | 9.63 ± 0.04 | 10.10 ± 0.05 | 9.18 ± 0.10 | 6.58 ± 0.21 | 9.42 ± 0.01 | 4.43 ± 0.03 | 8.71 ± 0.11 |
| | DPM | 10.13 ± 0.03 | 9.76 ± 0.02 | 10.15 ± 0.04 | 9.16 ± 0.15 | 7.41 ± 0.14 | 9.45 ± 0.04 | 4.70 ± 0.10 | 8.84 ± 0.05 |
| | DPFM | 10.24 ± 0.03 | 9.89 ± 0.01 | 10.23 ± 0.04 | 9.28 ± 0.12 | 7.68 ± 0.09 | 9.56 ± 0.06 | 5.46 ± 0.02 | 8.89 ± 0.03 |
| B3 | MRS | 9.24 ± 0.02 | 9.10 ± 0.05 | 9.30 ± 0.01 | 8.99 ± 0.05 | 7.32 ± 0.05 | 8.67 ± 0.47 | 4.43 ± 0.05 | 7.23 ± 0.61 |
| | DPM | 9.17 ± 0.02 | 9.02 ± 0.06 | 9.24 ± 0.03 | 8.95 ± 0.06 | 8.06 ± 0.06 | 8.90 ± 0.02 | 4.34 ± 0.05 | 7.95 ± 0.02 |
| | DPFM | 9.40 ± 0.02 | 9.19 ± 0.03 | 9.54 ± 0.01 | 9.02 ± 0.06 | 8.61 ± 0.03 | 9.08 ± 0.04 | 4.71 ± 0.52 | 7.97 ± 0.02 |
| B4 | MRS | 8.87 ± 0.03 | 8.64 ± 0.09 | 8.87 ± 0.03 | 8.64 ± 0.09 | 7.93 ± 0.03 | 8.21 ± 0.03 | 4.15 ± 0.05 | 6.89 ± 0.15 |
| | DPM | 9.04 ± 0.02 | 8.76 ± 0.03 | 9.04 ± 0.02 | 8.76 ± 0.03 | 8.00 ± 0.04 | 8.37 ± 0.02 | 4.42 ± 0.12 | 7.67 ± 0.04 |
| | DPFM | 9.15 ± 0.01 | 8.81 ± 0.07 | 9.15 ± 0.01 | 8.81 ± 0.07 | 8.05 ± 0.03 | 8.48 ± 0.01 | 4.51 ± 0.01 | 7.11 ± 0.01 |

Example 7

Determination of the Effect of $CaCl_2$ Concentration on Lactobacillus Growth

Five types of media were prepared: (1) MRS, (2) DPM (0.15 g/mL $CaCl_2$), (3) DPM (0.10 g/mL $CaCl_2$), (4) DPM (0.20 g/mL $CaCl_2$), and (5) DPM (0.30 g/mL $CaCl_2$). DPM was prepared by combining DPE with buffer solution (BS) containing different concentrations of $CaCl_2$. The composition of each Buffer solution preparation is shown in Table 7. Lactobacillus were cultivated in each of the five types of media for 24 hours. Percent growth was determined by counting the bacterial colonies and calculating the log CFU/mL for each sample following 48 hours of incubation at 37° C. As shown in Table 8, Lactobacillus growth in DPM was highest with use of buffer containing 0.2 g/L $CaCl_2$. The bacterial growth is comparable to growth in MRS.

TABLE 7

Buffer Solution Composition

| | BS (0.15 g/L $CaCl_2$) | BS (0.1 g/L $CaCl_2$) | BS (0.2 g/L $CaCl_2$) | BS (0.3 g/L $CaCl_2$) |
|---|---|---|---|---|
| L-Cysteine HCl | 1 | 1.5 | 1.5 | 1.5 |
| Na3PO4 | 2 | 2 | 2 | 2 |
| Ammonium citrate | 2 | 2 | 2 | 2 |
| NaCH3COOH Sodium acetate | 5 | 5 | 5 | 5 |
| CaCl2 | 0.15 | 0.1 | 0.2 | 0.3 |
| K2HPO4 | 2 | 2 | 2 | 2 |
| MgSO4 | 0.2 | 0.2 | 0.2 | 0.2 |
| MnSO4 | 0.05 | 0.05 | 0.05 | 0.05 |
| Tween 80 | 1 mL | 1 mL | 1 mL | 1 mL |

TABLE 8

Effect of $CaCL_2$ on Lactobacillus Growth

| Sample | MRS | BS (0.1 g/L $CaCl_2$) | BS (0.2 g/L $CaCl_2$) | BS (0.3 g/L $CaCl_2$) |
|---|---|---|---|---|
| Log CFU/mL | 9.72 | 8.90 | 9.27 | 9.10 |

TABLE 9

Comparison the bacterial growth of MRS and DPM by determination Cell Mass Log CFU/mL

| Sample | MRS | DPM with Original BS | DPM with Developed BS |
|---|---|---|---|
| Log CFU/mL | 9.79 | 9.15 | 10.30 |

Example 8

Determination of the Effect of TWEEN® 80 Concentrations on Lactobacillus Growth

Four types of media were prepared: (1) MRS, (2) DPM (1 mL/L TWEEN® 80), (3) DPM 2 mL/L TWEEN® 80), and (4) DPM (3 mL/L TWEEN® 80). DPM was prepared by combining DPE broth with buffer solution (BS). The composition of each buffer solution is shown in Table 10. Lactobacillus were cultivated in each of the five types of media for 24 hours. Percent growth was determined by counting the bacterial colonies and calculating the log CFU/mL for each sample following 24 hours of incubation at 37 C As shown in Table 11, Lactobacillus growth in DPM was highest with 3 mL/L TWEEN® 80. However, the bacterial growth did not reach the level of growth in MRS.

TABLE 10

Buffer Solution Composition

| | TWEEN® 80 (1 mL/L) | TWEEN® 80 (2 mL/L) | TWEEN® 80 (3 mL/L) |
|---|---|---|---|
| L-Cysteine HCl | 1 | 1.5 | 1.5 |
| Na3PO4 | 2 | 2 | 2 |
| Ammonium citrate | 2 | 2 | 2 |
| sodium acetate | 5 | 5 | 5 |
| CaCl2 | 0.15 | 0.3 | 0.3 |
| K2HPO4 | 2 | 2 | 2 |
| MgSO4 | 0.2 | 0.2 | 0.2 |
| MnSO4 | 0.05 | 0.05 | 0.05 |
| Tween 80 | 1 mL | 2 mL | 3 mL |

TABLE 11

Effect of TWEEN 80 on *Lactobacillus* Growth

| Sample | MRS | DPM (1 mL/L TWEEN® 80) | DPM (2 mL/L TWEEN® 80) | DPM (3 mL/L TWEEN® 80) |
|---|---|---|---|---|
| Log CFU/mL | 9.72 | 8.90 | 9.27 | 9.4 |

Example 9

Determination of the Effect of Optimized Buffer Solution (BS) on *Lactobacillus* Growth Three types of media were prepared: (1) MRS, (2) DPM (DPE+BS (0.15 g/L CaCl$_2$+1 mL/L TWEEN® 80)), (3) DPM (DPE+Optimized BS (0.2 g/L CaCl$_2$+3 mL/L TWEEN® 80)). Formulations for buffer solutions are shown in Table 12. *Lactobacillus* bacteria were incubated in each type of media at . Following 24 hours of incubation at 37° C., percent growth was determined by counting the bacterial colonies and calculating the log CFU/mL for each sample. As shown in Table 13, the DPM formulation with the optimized BS (0.2 g/L CaCl$_2$+3 mL/L TWEEN® 80) produced the highest cell growth.

TABLE 12

Buffer Solution Formulation

| | BS | Optimized BS |
|---|---|---|
| L-Cysteine HCl (g/L) | 1 | 1.5 |
| Na3PO4 (g/L) | 2 | 2 |
| Ammonium citrate (g/L) | 2 | 2 |
| sodium acetate (g/L) | 5 | 5 |
| CaCl2 (g/L) | 0.15 | 0.2 |
| K2HPO4 (g/L) | 2 | 2 |
| MgSO4 (g/L) | 0.2 | 0.2 |
| MnSO4 (g/L) | 0.05 | 0.05 |
| Tween 80 (mL/L) | 1 | 3 |

TABLE 13

Effects of DPM Formulation on Bacterial Growth

| Sample | MRS | DPE broth + Original BS | DPE broth + Optimized BS |
|---|---|---|---|
| Log CFU/mL | 9.79 | 9.15 | 10.30 |

Example 10

Effect of Date Palm Fiber (DPF) on the Morphological Characteristics of Bacteria Cells During the Fermentation Process In order to determine the impact of fiber on bacterial cell morphology, one bacterial strain of *Bifidobacterium bifidum* (B2) was cultivated in three broth media: (1) MRS broth, (2) DPM and (3) DPFM. Scanning electron microscopy was used to visualize the adherence of B2 to fiber in vitro according to the methods described in Hood, S. K. and Zottola, E. A. (1989) An Electron Microscopic Study of the Adherence of *Lactobacillus Acidophilus* to Human Intestinal Cells in Vitro. *Food Structure*, 8:91-97. Briefly, B2 was cultivated in each of the three broth media for 16-18 hours at 37° C. To examine the cellular morphology of cells growing in broth, the bacterial cells were collected by centrifugation (3000×g for 10 min) and prepared for electron microscopy.

Figure 2:
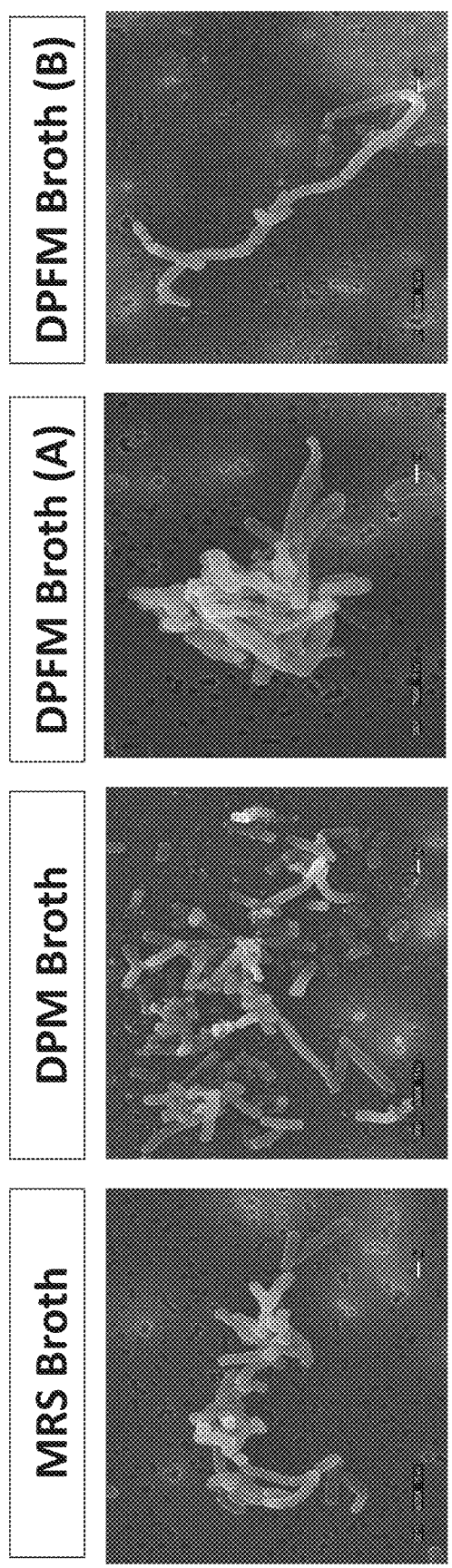
FIG. 2 shows scanning electron microscopy (SEM) images of *Bifidobacterium bifidum* (B2) cultivated in three types of broth media (MRS broth, DPM and DPFM).

As shown in FIG. 2, bacteria incubated in DPFM are coated in a layer of fibers, which serve as a protective material for bacterial cells during fermentation. The bacterial cells grown in DPFM were able to aggregate, which is beneficial during the freeze-drying process. Incubation in MRS broth resulted in small, short, and thin bacterial cells that were cylindrical with few curves. MRS-cultured bacterial cells formed small aggregates with a smooth cell surface. Conversely, bacterial cells grown in DPM broth were large, long, thin, curved bacterial cells. DPM-cultured cells were generally grouped into "Y" shapes and formed several small groups of aggregates around particles and tended to have rougher surfaces. Bacterial cells grown in DPFM were large, long, thick, puffed bacterial cells. (FIG. 2 DPFM Broth (A)). DPFM-cultured cells formed long chains with curves and some aggregates (FIG. 2 DPFM Broth (B)). The surface of the cells grown in DPFM tended to be rough. These images suggest that bacterial cells cultured in DPFM are able to adhere to the fiber component of the media. The results indicates that the fiber is able to coat bacterial cells, which provides a protective layer for bacterial cells during the fermentation process and allow the bacterial cells to form aggregates. The formation of aggregates is important for the protection of bacterial cells during processing steps (e.g., freeze-drying) that are commonly used for probiotics.

Example 11

Demonstration of Suitability of Phytone Peptone (PP) and Yeast Extract (YE) as Nitrogen Source for Multiple Strains of Bacterial Growth in DPM Preparation of date palm extract broth: Date palm paste (40 Kg) was added to water (60 Kg) in a high shear mixer and agitated at 75° C. for 1 h. The dispersion was then milled using a colloid mill three times before subjecting to homogenization. The dispersion was then diluted with water (148 Kg) and soaked for 16 h at 4° C. The diluted dispersion was then transferred to a decanter and supernatant was collected. Thus, the obtained supernatant was sterilized via ultra-high temperature treatment at 142° C. for 14 seconds and stored the date palm extract broth at 4° C. for future use.

Preparation of Buffer: A buffer solution was prepared by dissolving ingredients listed in the Table 14 below in 1500 mL of water.

TABLE 14

Buffer solution composition

| Name of the ingredient | Quantity used (g per 1.5 liter) |
|---|---|
| L-cysteine-hydrochloride | 2.28 |
| KH$_2$PO$_4$ | 3.45 |
| Ammonium citrate | 2.99 |
| Sodium acetate | 7.5 |
| CaCl$_2$ | 0.5 |
| K$_2$HPO$_4$ | 3 |
| Magnesium sulfate heptahydrate | 0.64 |
| Manganese sulfate tetrahydrate | 0.08 |
| Arginine | 0.77 |
| Tween 80 | 4.51 |
| Water | 1500 |

Preparation of phytone peptone solution: A phytone peptone solution was prepared by dissolving 16 g of phytone peptone in 135 mL of water and sterilized via ultra-high temperature treatment at 142° C. for 14 seconds.

Preparation of yeast extract solution: A yeast extract solution was prepared by dissolving 16 g of Yeast Extract in 135 mL of water and sterilized via ultra-high temperature treatment at 142° C. for 14 seconds.

Preparation of date palm medium containing Phytone Peptone (Med 1 PP): DPM containing phytone peptone was prepared by mixing date palm extract (900 mL), buffer solution (600 mL) and phytone peptone solution (120 mL). Thus obtained Med 1-PP is sterilized via ultra-high temperature treatment at 142° C. for 14 seconds.

Preparation of date palm medium containing Yeast Extract (Med 2 YE): Prepared by mixing date palm extract (900 mL), buffer solution (600 mL) and Yeast Extract solution (120 mL). Obtained Med 2-YE was sterilized via ultra-high temperature treatment at 142° C. for 14 seconds.

Figure 3:
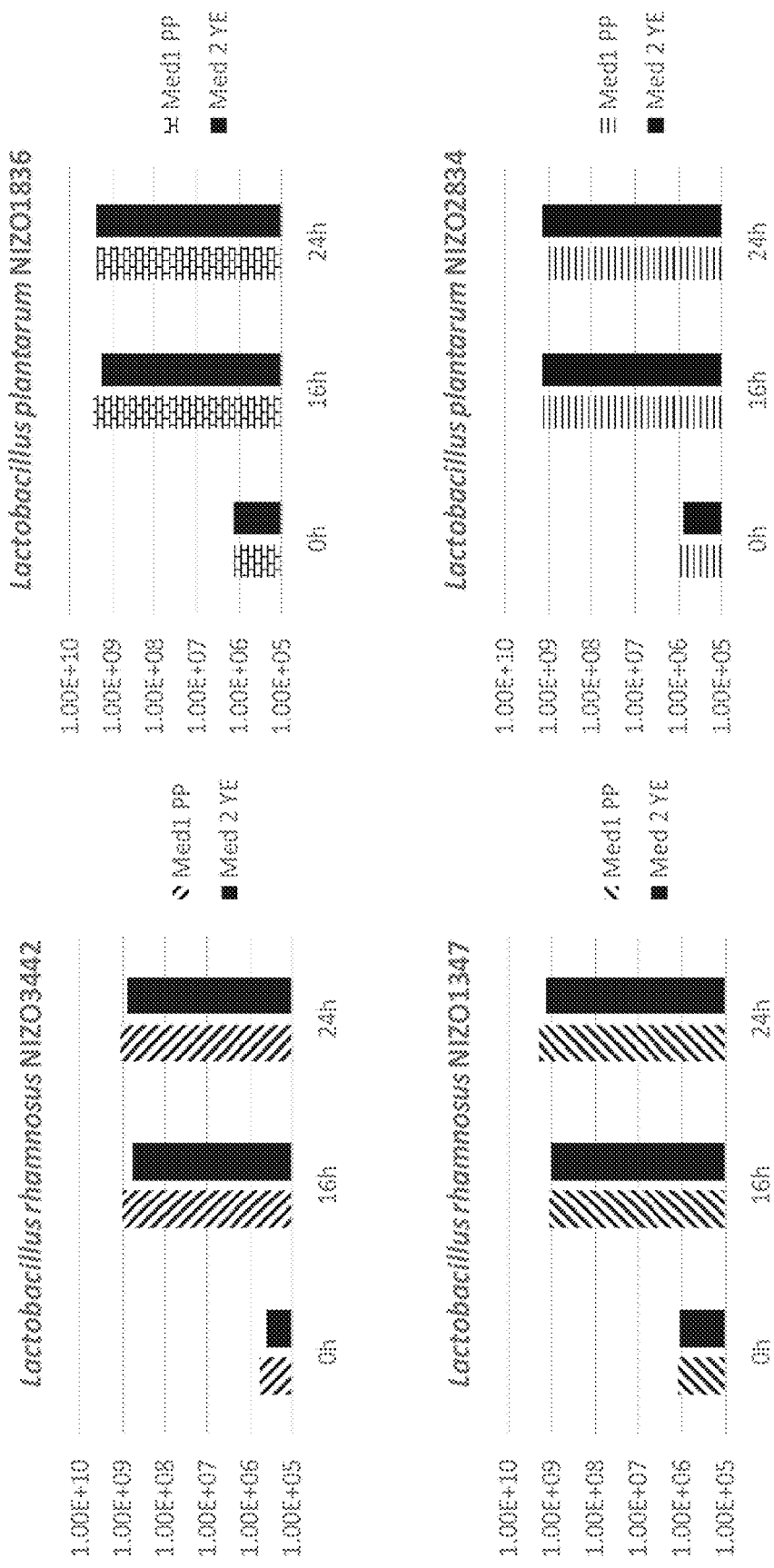
FIG. 3 shows compatibility of Phytone Peptone or Yeast Extract as nitrogen source with DPM prepared from date paste as bacterial growth media.

Cultivation of bacteria in DPM with Phytone Peptone or Yeast Extract as nitrogen source: Four laboratory scale autoclaved bioreactors equipped with pH monitors were charged with 200 mL each with Med 1-PP and *Lactobacillus rhamnosus* NIZO3442, *Lactobacillus rhamnosus* NIZO 1347, *Lactobacillus plantarum* NIZO1836 and *Lactobacillus plantarum* NIZO2834 strains are inoculated separately and incubated at 37° C. for 24 h. Similarly, four laboratory scale autoclaved bioreactors equipped with pH monitors were charged with Med 2-YE and *Lactobacillus rhamnosus* NIZO3442, *Lactobacillus rhamnosus* NIZO 1347, *Lactobacillus plantarum* NIZO1836 and *Lactobacillus plantarum* NIZO2834 strains are inoculated separately and incubated at 37° C. for 24 h. Growth of each strain with both nitrogen sources was similar in magnitude as shown in FIG. 3.

Example 12

Demonstration of Suitability of DPFM from Date Paste without Filtration or without Added DPF Preparation of date palm extract broth with DPF: Date palm paste (150 g) was added to water (1000 mL) and heated at 60° C. for 3 h to obtain a slurry mixture. The slurry mixture is soaked for 16 h at 4° C. Thus obtained slurry is sterilized by autoclaving at 118° C. for 15 minutes and stored the date palm extract broth with fibers at 4° C. for future use.

Preparation of Buffer containing 0.8% Yeast extract: A buffer solution is prepared by dissolving ingredients listed in the Table 15 below in 1000 mL of water. Thus obtained buffer is sterilized by autoclaving at 118° C. for 15 minutes and pH is found to be 6.97.

TABLE 15

| Buffer solution composition | |
| --- | --- |
| Name of the ingredient | Quantity used (g per1.0 liter) |
| L-cysteine-hydrochloride | 1.5 |
| $Na_3PO_4$ | 2 |
| Ammonium citrate | 2 |
| Sodium acetate | 5 |
| $CaCl_2$ | 0.3 |
| $K_2HPO_4$ | 2 |
| Magnesium sulfate heptahydrate | 0.2 |
| Manganese sulfate tetrahydrate | 0.05 |
| Arginine | 0.5 |
| Tween 80 | 3 |
| Yeast extract (YE) | 8 |
| Water | 1000 |

Preparation of DPMF containing Yeast Extract: Prepared by mixing sterilized date palm extract broth with fiber (1200 mL) and sterilized buffer solution containing 0.8% Yeast Extract (800 mL).

Cultivation of bacteria in DPFM with Yeast Extract as nitrogen source: Two autoclaved 250 mL culture bottles are charged 200 mL each with DPFM containing yeast extract and inoculated with 200 micro liters of stock solution (1:1 water-glycerol) of *Lactobacillus rhamnosus* (LGG) and *Bifidobacterium bifidum* (B2) in to separate bottles. The cultures were incubated at 37° C. for 24 h. Growth of each strain wass monitored at regular intervals (Table 16).

TABLE 16

| Growth of B2 and LGG in DPFM at 37° C. for 24 h | | | | | |
| --- | --- | --- | --- | --- | --- |
| | Time/h | | | | |
| | 0 | 3 | 6 | 12 | 24 |
| | Log CFU/mL | | | | |
| Bottle 1 (LGG) | 6.59 | 6.59 | 7.21 | 8.26 | 11.11 |
| Bottle 2 (B2) | 6.57 | 7.03 | 8.14 | 9.22 | 11.09 |

Example 13

Illustrative Embodiments

As used below, any reference to methods, products, or systems is understood as a reference to each of those methods, products, or systems disjunctively (e.g., "Illustrative embodiment 1-4 is understood as illustrative embodiment 1, 2, 3, or 4.").

A.1 Illustrative embodiment 1 is a method of preparing a date palm extract (DPE) broth comprising: (i) obtaining a mass of date material; (ii) combining the date material with a suspension liquid to produce a slurry mixture; (iii) processing the slurry mixture to produce a date palm extract broth with fibers (DPEF); and (iv) separating the DPEF into the DPE broth and a mass of date palm fiber (DPF).

A.2 Illustrative embodiment 2 is the method of preparing a date palm extract (DPE) broth of any preceding or subsequent illustrative embodiment, wherein the date material comprises a date paste.

A.3 Illustrative embodiment 3 is the method of preparing a date palm extract (DPE) broth of any preceding or subsequent illustrative embodiment, wherein the date paste is cubed.

A.4 Illustrative embodiment 4 is the method of preparing a date palm extract (DPE) broth of any preceding or subsequent illustrative embodiment, wherein the date material comprises a date presscake.

A.5 Illustrative embodiment 5 is the method of preparing a date palm extract (DPE) broth of any preceding or subsequent illustrative embodiment, wherein the date presscake is formed by applying an amount of pressure to a mass of date fruit to extract liquid therefrom.

A.6 Illustrative embodiment 6 is the method of preparing a date palm extract (DPE) broth of any preceding or subsequent illustrative embodiment, wherein the date fruit is in the kimiri, or khala, or rutab, or tamer stage of ripening.

A.7 Illustrative embodiment 7 is the method of preparing a date palm extract (DPE) broth of any preceding or subsequent illustrative embodiment, wherein the processing step comprises at least one heating period, at least one milling period, and at least one soaking period.

A.8 Illustrative embodiment 8 is the method of preparing a date palm extract (DPE) broth of any preceding or subsequent illustrative embodiment, wherein the heating period comprises mixing the slurry mixture while heating the slurry mixture to a temperature of at least 60° C. for at least 3 hours.

A.9 Illustrative embodiment 9 is the method of preparing a date palm extract (DPE) broth of any preceding or subsequent illustrative embodiment, wherein the slurry mixture is mixed under high shear agitation.

A.10 Illustrative embodiment 10 is the method of preparing a date palm extract (DPE) broth of any preceding or subsequent illustrative embodiment, wherein the milling period comprises milling the heated slurry mixture using a colloid mill.

A.11 Illustrative embodiment 11 is the method of preparing a date palm extract (DPE) broth of any preceding or subsequent illustrative embodiment, wherein the soaking period comprises diluting the milled slurry mixture with the suspension liquid and cooling the diluted, milled slurry mixture at 4° C. for at least 12 hours.

A.12 Illustrative embodiment 12 is the method of preparing a date palm extract (DPE) broth of any preceding or subsequent illustrative embodiment, wherein the processing step comprises: (i) a heating period comprising mixing the slurry mixture under high shear agitation while heating the slurry mixture to a temperature between 65° C. and 80° C. for between 45 and 90 minutes; (ii) a milling period comprising milling the heated slurry mixture three times using a colloid mill; and (iii) a soaking period comprising diluting the milled slurry mixture with the suspension liquid and cooling the diluted, milled slurry mixture at 4° C. for at least 12 hours.

A.13 Illustrative embodiment 13 is the method of preparing a date palm extract (DPE) broth of any preceding or subsequent illustrative embodiment, wherein the processing step comprises three or more heating periods and two or more soaking periods.

A.14 Illustrative embodiment 14 is the method of preparing a date palm extract (DPE) broth of any preceding or subsequent illustrative embodiment, wherein the soaking period comprises mixing the heated slurry mixture while it is cooled at 4° C. for at least 18 hours.

A.15 Illustrative embodiment 15 is the method of preparing a date palm extract (DPE) broth of any preceding or subsequent illustrative embodiment, wherein the heating period comprises heating the slurry mixture to a temperature from 50° C. and 70° C. for between 10 and 20 minutes.

A.16 Illustrative embodiment 16 is the method of preparing a date palm extract (DPE) broth of any preceding or subsequent illustrative embodiment, wherein the processing step comprises: (i) a first heating period comprising heating the slurry mixture to a temperature from between 50° C. and 70° C. for between 10 and 20 mins; (ii) a first soaking period comprising mixing the heated slurry mixture while being cooled at 4° C. for at least 18 hours; (iii) a second heating period comprising heating the slurry mixture to a temperature from between 50° C. and 70° C. for between 10 and 20 mins; (iv) a second soaking period comprising mixing the heated slurry mixture while being cooled at 4° C. for at least 18 hours; and (v) a third heating period comprising heating the slurry mixture to a temperature from 50° C. and 70° C. for between 10 and 20 mins.

A.17 Illustrative embodiment 17 is the method of preparing a date palm extract (DPE) broth of any preceding or subsequent illustrative embodiment, wherein the slurry mixture is separated into the DPE broth and the mass of DPF using a decanter.

A.18 Illustrative embodiment 18 is the method of preparing a date palm extract (DPE) broth of any preceding or subsequent illustrative embodiment, wherein the slurry mixture is separated into the DPE broth and the mass of DPF using a filter.

A.19 Illustrative embodiment 19 is the method of preparing a date palm extract (DPE) broth of any preceding or subsequent illustrative embodiment, wherein the filter is a cheesecloth.

A.20 Illustrative embodiment 20 is the method of preparing a date palm extract (DPE) broth of any preceding or subsequent illustrative embodiment, wherein the DPE broth is sterilized.

A.21 Illustrative embodiment 21 is the method of preparing a date palm extract (DPE) broth of any preceding or subsequent illustrative embodiment, wherein the A.22 Illustrative embodiment 22 is a method of preparing a date palm medium (DPM) for culturing microorganisms comprising: (i) preparing a buffer solution; (ii) buffering a date palm extract (DPE) broth with the buffer solution, wherein the DPE broth is prepared according to the method of any preceding or subsequent illustrative embodiment; and (iii) adding a nitrogen source from non-animal origin to the buffered DPE broth.

A.23 Illustrative embodiment 23 is a method of preparing a date palm medium (DPM) for culturing microorganisms comprising: (i) preparing a buffer solution; (ii) buffering a date palm extract (DPE) broth with the buffer solution, wherein the DPE broth is prepared according to the method of claim 1; (iii) adding an amount of date palm fiber (DPF), wherein the DPF is isolated according to the method of any preceding or subsequent illustrative embodiment; and (iv) adding a nitrogen source from non-animal origin to the buffered DPE broth.

A.24 Illustrative embodiment 24 is a method of preparing a date palm medium with fiber (DPFM) for culturing microorganisms comprising: (i) preparing a buffer solution; (ii) buffering a date palm extract broth with fibers (DPEF) with the buffer solution, wherein the DPEF is prepared according to the method of any preceding or subsequent illustrative embodiment; and (iii) adding a nitrogen source from non-animal origin to the buffered DPEF.

A.25 Illustrative embodiment 25 is a method of any preceding or subsequent illustrative embodiment, wherein the buffer solution is prepared by combining L-cysteine hydrochloride, sodium phosphate, ammonium citrate, sodium acetate, calcium chloride, potassium phosphate, magnesium sulfate heptahydrate, manganese sulfate tetrahydrate, arginine, TWEEN-80®, and deionized water.

A.26 Illustrative embodiment 26 is a method of any preceding or subsequent illustrative embodiment, wherein the concentration of calcium chloride is at least 0.2 g/L.

A.27 Illustrative embodiment 27 is a method of any preceding or subsequent illustrative embodiment, wherein the concentration of TWEEN-80® is at least 2 mL/L.

A.28 Illustrative embodiment 28 is a method of any preceding or subsequent illustrative embodiment, wherein the pH of the buffer solution is from about 5.5-6.2.

A.29 Illustrative embodiment 29 is a method of any preceding or subsequent illustrative embodiment, wherein the buffering step comprises combining the buffer solution and the DPE or DPEF solution in a volume to volume ratio of 2:3.

A.30 Illustrative embodiment 30 is a method of any preceding or subsequent illustrative embodiment, wherein the nitrogen source comprises a peptone, tryptone, proteose peptone, phytone peptone, polypeptone peptonetryptic soy broth, or a yeast extract.

A.31 Illustrative embodiment 31 is a method of any preceding or subsequent illustrative embodiment, wherein the nitrogen source is a phytone peptone.

A.32 Illustrative embodiment 32 is a method of any preceding or subsequent illustrative embodiment, wherein the additional growth factors for culturing microorganisms in growth media are added A.33 Illustrative embodiment 33 is a method of any preceding or subsequent illustrative embodiment, wherein the selective components are added to the medium.

A.34 Illustrative embodiment 34 is a method of any preceding or subsequent illustrative embodiment, wherein the differential components are added to the medium.

A.35 Illustrative embodiment 35 is a method of any preceding or subsequent illustrative embodiment, wherein the DPM or DPFM is sterilized.

A.36 Illustrative embodiment 36 is a method of any preceding or subsequent illustrative embodiment, wherein an amount of fiber is added to the DPM or DPFM.

A.37 Illustrative embodiment 37 is a method of any preceding or subsequent illustrative embodiment, wherein the nitrogen source is added to the buffered DPE in a volume to volume ratio of nitrogen source to buffered DPE of about 2:25.

A.38 Illustrative embodiment 38 is a medium for culturing microorganisms comprising: (i) a buffered date palm extract (DPE), wherein the DPE is prepared according to the method of any preceding or subsequent illustrative embodiment; and (ii) a nitrogen source.

A.39 Illustrative embodiment 39 is a medium for culturing microorganisms comprising: (i) a buffered date palm extract (DPE), wherein the DPE is prepared according to the method of any preceding or subsequent illustrative embodiment (ii) an amount of date palm fiber (DPF); and (iii) a nitrogen source.

A.40 Illustrative embodiment 40 is a medium for culturing microorganisms of any preceding or subsequent illustrative embodiment, wherein the volume to volume ratio of buffer solution to DPE solution is about 2:3.

A.41 Illustrative embodiment 41 is a medium for culturing microorganisms of any preceding or subsequent illustrative embodiment, wherein the volume to volume ratio of nitrogen source to buffered DPE of about 2:25.

A.42 Illustrative embodiment 42 is a medium for culturing microorganisms of any preceding or subsequent illustrative embodiment, wherein the buffer solution used to buffer DPE comprises L-cysteine hydrochloride, sodium phosphate, ammonium citrate, sodium acetate, calcium chloride, potassium phosphate, magnesium sulfate, manganese sulfate, arginine, TWEEN® 80, and deionized water.

A.43 Illustrative embodiment 43 is a medium for culturing microorganisms of any preceding or subsequent illustrative embodiment, wherein the concentration of calcium chloride in the buffer solution is at least 0.2 g/L.

A.44 Illustrative embodiment 44 is a medium for culturing microorganisms of any preceding or subsequent illustrative embodiment, wherein the concentration of TWEEN® 80 in the buffer solution is at least 2 mL/L.

A.45 Illustrative embodiment 45 is a medium for culturing microorganisms of any preceding or subsequent illustrative embodiment, wherein the medium is capable of cultivating microorganisms.

A.46 Illustrative embodiment 46 is a method of cultivating microorganisms comprising: (i) inoculating the date palm medium (DPM) of any of the preceding or subsequent illustrative embodiments with microorganisms; and (ii) incubating the microorganisms under conditions such that growth occurs.

A.47 Illustrative embodiment 47 is a method of cultivating microorganisms comprising: (i) inoculating a date palm medium plus fiber (DPFM) of any of the preceding or subsequent claims with microorganisms; and (ii) incubating the microorganisms under conditions such that growth occurs.

A.48 Illustrative embodiment 48 is a method of any of the preceding or subsequent illustrative embodiments, wherein the DPM or DPFM comprises a buffered date palm extract (DPE), wherein the DPE is prepared according to the method of any of the preceding or subsequent illustrative embodiments.

A.49 Illustrative embodiment 49 is a method of any of the preceding or subsequent illustrative embodiments, wherein the volume to volume ratio of buffer solution to DPE solution is about 2:3.

A.50 Illustrative embodiment 50 is a method of any of the preceding or subsequent illustrative embodiments, wherein the DPM or DPFM comprises a nitrogen source.

A.51 Illustrative embodiment 51 is a method of any of the preceding or subsequent illustrative embodiments, wherein the volume to volume ratio of nitrogen source to buffered DPE of about 2:25.

A.52 Illustrative embodiment 52 is a method of any of the preceding or subsequent illustrative embodiments, wherein an amount of DPF, wherein the DPF isolated according to the method any of the preceding or subsequent embodiments, is added to the DPM 24 hours post inoculation.

A.53 Illustrative embodiment 53 is a method of any of the preceding or subsequent illustrative embodiments, wherein the microorganisms are bacteria.

A.54 Illustrative embodiment 54 is a method of any of the preceding or subsequent illustrative embodiments, wherein the bacteria is Gram-positive or Gram-negative or combinations thereof.

A.55 Illustrative embodiment 55 is a method of any of the preceding or subsequent illustrative embodiments, wherein the bacteria is at least one of a *Lactobacillus* species or a *Bifidobacterium* species.

A.56 Illustrative embodiment 55 is a method of any of the preceding or subsequent illustrative embodiments, wherein the DPM or DPFM is inoculated with 1-2% microorganism by volume.

A.57 Illustrative embodiment 57 is a method of any of the preceding or subsequent illustrative embodiments, wherein the cultivated microorganism is used in a probiotic.

A.58 Illustrative embodiment 58 is a method of any of the preceding or subsequent illustrative embodiments, wherein the probiotic is used as food or nutritional supplement.

A.59 Illustrative embodiment 59 is a probiotic comprising bacteria cultivated in the medium of any one of the preceding or subsequent illustrative embodiments.

A.60 Illustrative embodiment 60 is a probiotic of any of the preceding or subsequent illustrative embodiments, wherein the bacteria is at least one of a *Lactobacillus* species or a *Bifidobacterium* species.

A.61 Illustrative embodiment 61 is a probiotic of any of the preceding or subsequent illustrative embodiments, wherein the probiotic is a dietary supplement or a food supplement.

What is claimed is:

1. A method of cultivating microorganisms comprising:
   (i) inoculating a culture medium comprising date fruit presscake with microorganisms; and
   (ii) incubating the microorganisms.

2. A method of cultivating microorganisms comprising:
   (i) inoculating culture medium comprising date fruit presscake and date fruit fiber with microorganisms; and
   (ii) incubating the microorganisms.

3. The method of claim 2, wherein the microorganisms are bacteria.

4. The method of claim 3, wherein the bacteria is at least one of a *Lactobacillus* species or a *Bifidobacterium* species.

5. The method of claim 2, wherein the culture medium is inoculated with 1-2% microorganisms by volume.

* * * * *